(12) United States Patent
Agrawal et al.

(10) Patent No.: US 12,697,173 B2
(45) Date of Patent: Aug. 4, 2026

---

(54) METHOD, DEVICE AND SYSTEM TO DETERMINE A FREQUENCY FUNCTION OF A BASILAR MEMBRANE OF COCHLEAE TO TUNE COCHLEAR IMPLANTS

(71) Applicant: MED-EL ELEKTROMEDIZINISCHE GERAETE GMBH, Innsbruck (AT)

(72) Inventors: Sumit Agrawal, London (CA); Hanif Ladak, London (CA)

(73) Assignee: MED-EL ELEKTROMEDIZINISCHE GERAETE GMBH, Innsbruck (AT)

( * ) Notice: Subject to any disclaimer, the term of this patent is extended or adjusted under 35 U.S.C. 154(b) by 377 days.

(21) Appl. No.: 18/292,407

(22) PCT Filed: Jul. 29, 2021

(86) PCT No.: PCT/IB2021/056935
§ 371 (c)(1),
(2) Date: Jan. 26, 2024

(87) PCT Pub. No.: WO2023/007227
PCT Pub. Date: Feb. 2, 2023

(65) Prior Publication Data
US 2024/0249425 A1     Jul. 25, 2024

(51) Int. Cl.
*A61B 34/10*          (2016.01)
*G06T 3/40*           (2006.01)
(Continued)

(52) U.S. Cl.
CPC ................ *A61B 34/10* (2016.02); *G06T 3/40* (2013.01); *G06T 7/0016* (2013.01); *G06T 7/11* (2017.01);
(Continued)

(58) Field of Classification Search
CPC ......... A61B 5/12; A61B 5/6817; A61B 34/10; A61N 1/36038; G06T 7/0016; G06T 7/11;
(Continued)

(56) References Cited

U.S. PATENT DOCUMENTS 8,565,889 B2    10/2013   Spitzer
10,546,388 B2    1/2020   Noble et al.
(Continued)

FOREIGN PATENT DOCUMENTS

WO     2021041236 A1    3/2021
WO     2021041466 A1    3/2021

OTHER PUBLICATIONS

International Search Report, mailed Apr. 7, 2022, issued in corresponding PCT Application No. PCT/IB2021/056935, filed Jul. 29, 2021.
(Continued)

*Primary Examiner* — Daniel G Mariam
(74) *Attorney, Agent, or Firm* — PERRY + CURRIER INC.

(57)          ABSTRACT

A device, system and method to determine a frequency function of a basilar membrane of cochleae to tune cochlear implants is provided. A clinically available scan of a cochlea of a given format is input to a machine learning engine trained to: output higher resolution cochlear images of a resolution higher than the given format using input based on clinically available cochlear scans of the given format. A higher resolution image of the cochlea is determined using the machine learning engine. A number of turns of the cochlea is determined from the higher resolution image. A frequency function of a basilar membrane of the cochlea is determined and/or output, the frequency function being dependent on an angle of the basilar membrane. The fre-
(Continued)

quency function is determined and/or output by inputting the number of turns into a generic predetermined frequency function dependent on the number of turns and the angle.

20 Claims, 7 Drawing Sheets

(51) Int. Cl.
| | |
|---|---|
| *G06T 7/00* | (2017.01) |
| *G06T 7/11* | (2017.01) |
| *G06T 7/13* | (2017.01) |
| *G06T 7/30* | (2017.01) |
| *G06T 7/60* | (2017.01) |
| *G06T 7/70* | (2017.01) |

(52) U.S. Cl.
CPC .................. *G06T 7/13* (2017.01); *G06T 7/30* (2017.01); *G06T 7/60* (2013.01); *G06T 7/70* (2017.01); *G06T 2207/10081* (2013.01); *G06T 2207/20081* (2013.01); *G06T 2207/30052* (2013.01); *G06T 2207/30242* (2013.01)

(58) Field of Classification Search
CPC .... G06T 7/13; G06T 7/30; G06T 7/60; G06T 7/70; G06T 3/40; G06T 2207/10081; G06T 2207/20081; G06T 2207/30052; G06T 2207/30242
See application file for complete search history.

(56) References Cited

U.S. PATENT DOCUMENTS

| | | | |
|---|---|---|---|
| 10,821,284 | B2 | 11/2020 | Noble et al. |
| 12,499,986 | B2 * | 12/2025 | Avci ..................... A61N 1/0541 |
| 2015/0088225 | A1 | 3/2015 | Noble et al. |
| 2015/0379723 | A1 | 12/2015 | Reda et al. |
| 2019/0325621 | A1 | 10/2019 | Wang et al. |
| 2020/0279411 | A1 | 9/2020 | Atria et al. |

OTHER PUBLICATIONS

Jiam, Nicole T., et al. "Association between flat-panel computed tomographic imaging-guided place-pitch mapping and speech and pitch perception in Cochlear implant users." JAMA Otolaryngology—Head & Neck Surgery 145.2 (2019): 109-116.
Alexiades, George et al. "Method to estimate the complete and two-turn cochlear duct length." Otology & Neurotology 36.5 (2015): 904-907.
Erixon, Elsa et al. "How to predict cochlear length before cochlear implantation surgery." Acta oto-laryngologica 133.12 (2013): 1258-1265.
Koch, Robert W., et al. "Evaluation of cochlear duct length computations using synchrotron radiation phase-contrast imaging." Otology & Neurotology 38.6 (2017): e92-e99.
Erixon, Elsa, et al. "Variational anatomy of the human cochlea: implications for cochlear implantation." Otology & Neurotology 30.1 (2009): 14-22.
Iyaniwura, John E., et al. "Intra- and interobserver variability of cochlear length measurements in clinical CT." Otology & Neurotology 38.6 (2017): 828-832.
Schurzig, Daniel, et al. "A cochlear scaling model for accurate anatomy evaluation and frequency allocation in cochlear implantation." Hearing Research 403 (2021): 108166.
Pietsch, Marcus, et al. "Spiral form of the human cochlea results from spatial constraints." Scientific reports 7.1 (2017): 7500.
Stakhovskaya, Olga, et al. "Frequency map for the human cochlear spiral ganglion: implications for cochlear implants." Journal for the Association for Research in Otolaryngology 8 (2007): 220-233.
Schurzig, Daniel, et al. "A novel method for clinical cochlear duct length estimation toward patient-specific cochlear implant selection." OTO open 2.4 (2018): 2473974X18800238.
Escude, Bernard, et al. "The size of the cochlea and predictions of insertion depth angles for cochlear implant electrodes." Audiology and Neurotology 11.Suppl. 1 (2006): 27-33.
Noble, Jack H., et al. "Automatic segmentation of intracochlear anatomy in conventional CT." IEEE Transactions on Biomedical Engineering 58.9 (2011): 2625-2632.
Rivas, Alejandro, et al. "Automatic cochlear duct length estimation for selection of cochlear implant electrode arrays." Otology & neurotology: official publication of the American Otological Society, American Neurotology Society [and] European Academy of Otology and Neurotology 38.3 (2017): 339.
CTV News, "New tool helps cochlear implant patients hear with improved clarity", ctvnews.ca, May 31, 2021, London, URL: https://london.ctvnews.ca/new-tool-helps-cochlear-implant-patients-hear-with-improved-clarity-1.5450656, Retrieved from the Internet on Oct. 3, 2024.
Shaw Spotlight, "Hearing through light", youtube.com, Sep. 9, 2019, URL: https://www.youtube.com/watch?v=7U6uZiH6wB0, Retrieved from the Internet on Feb. 20, 2024.
Wilson, Katherine, et al. "Cochlear implant assessment and candidacy for children with partial hearing." Cochlear Implants International 17.sup1 (2016): 66-69.
Fitzpatrick, Elizabeth M. et al., "Adult Cochlear Implantation in Canada: Results of a Survey Implantation cochléaire chez les adultes au Canada: Résultats d'une enquête." Revue canadienne d'orthophonie et d'audiologie—vol. 34.4 (2010): 290.
Landsberger, David M., et al. "The relationship between insertion angles, default frequency allocations, and spiral ganglion place pitch in cochlear implants." Ear and hearing 36.5 (2015): e207-e213.
Tan, Chin-Tuan et al., "Pitch matching between electrical stimulation of a cochlear implant and acoustic stimuli presented to a contralateral ear with residual hearing." Journal of the American Academy of Audiology 28.03 (2017): 187-199.
Canfarotta, Michael W., et al. "Influence of age at cochlear implantation and frequency-to-place mismatch on early speech recognition in adults." Otolaryngology—Head and Neck Surgery 162.6 (2020): 926-932.
Kan, Alan et al. "Effects of interaural pitch-matching and auditory image centering on binaural sensitivity in cochlear-implant users." Ear and hearing 36.3 (2015): e62.
Greenwood, Donald D. "A cochlear frequency-position function for several species—29 years later." The Journal of the Acoustical Society of America 87.6 (1990): 2592-2605.
Svirsky, Mario A., et al. "Bilateral cochlear implants with large asymmetries in electrode insertion depth: implications for the study of auditory plasticity." Acta oto-laryngologica 135.4 (2015): 354-363.
Feder Katya P., et al. "Prevalence of hearing loss among Canadians aged 20 to 79: Audiometric results from the 2012/2013 Canadian Health Measures Survey." (2015).
Zeng, Fan-Gang et al., "Abnormal pitch perception produced by cochlear implant stimulation." PloS one 9.2 (2014): e88662.
Peters, Jeroen PM et al., "Comparison of place-versus-pitch mismatch between a perimodiolar and lateral wall cochlear implant electrode array in patients with single-sided deafness and a cochlear implant." Audiology and Neurotology 24.1 (2019): 38-48.
Dorman, Michael F., et al. "Looking for Mickey Mouse™ but finding a munchkin: The perceptual effects of frequency upshifts for single-sided deaf, cochlear implant patients." Journal of Speech, Language, and Hearing Research 62.9 (2019): 3493-3499.
Caldwell, Meredith T. et al., "Assessment and improvement of sound quality in cochlear implant users." Laryngoscope investigative otolaryngology 2.3 (2017): 119-124.
Limb, Charles J et al. "Technological, biological, and acoustical constraints to music perception in cochlear implant users." Hearing research 308 (2014): 13-26.
Reiss, Lina AJ, et al. "Plasticity in human pitch perception induced by tonotopically mismatched electro-acoustic stimulation." Neuroscience 256 (2014): 43-52.

(56) References Cited

OTHER PUBLICATIONS

Noble, Jack H., et al. "Statistical shape model segmentation and frequency mapping of cochlear implant stimulation targets in CT." Proceedings of the 15th international conference on Medical Image Computing and Computer-Assisted Intervention—vol. Part II. 2012.

Zhao, Yiyuan, et al. "Automatic graph-based method for localization of cochlear implant electrode arrays in clinical CT with sub-voxel accuracy." Medical image analysis 52 (2019): 1-12.

Van Der Jagt, Annerie MA., et al. "Variations in cochlear duct shape revealed on clinical CT images with an automatic tracing method." Scientific Reports 7.1 (2017): 17566.

Nikan, Soodeh, et al. "PWD-3DNet: a deep learning-based fully-automated segmentation of multiple structures on temporal bone CT scans." IEEE Transactions on Image Processing 30 (2020): 739-753.

Li, Hao, et al. "Three-dimensional tonotopic mapping of the human cochlea based on synchrotron radiation phase-contrast imaging." Scientific reports 11.1 (2021): 4437.

Helpard, Luke, et al. "Characterization of the human helicotrema: implications for cochlear duct length and frequency mapping." Journal of Otolaryngology—Head & Neck Surgery 49.1 (2020): 2.

Helpard, Luke, et al. "Three-dimensional modeling and measurement of the human cochlear hook region: Considerations for tonotopic mapping." Otology & Neurotology 42.6 (2021): e658-e665.

Helpard, Luke W., et al. "Evaluation of cochlear duct length measurements from a 3D analytical cochlear model using synchrotron radiation phase-contrast imaging." Otology & Neurotology 41.1 (2020): e21-e27.

Elfarnawany, M., et al. "Micro-CT versus synchrotron radiation phase contrast imaging of human cochlea." Journal of microscopy 265.3 (2017): 349-357.

Iyaniwura, John E., et al. "An automated A-value measurement tool for accurate cochlear duct length estimation." Journal of Otolaryngology—Head & Neck Surgery 47.1 (2018): 5.

Pichat, Jonas, et al. "A survey of methods for 3D histology reconstruction." Medical image analysis 46 (2018): 73-105.

Helpard, Luke, et al. "An approach for individualized cochlear frequency mapping determined from 3D synchrotron radiation phase-contrast imaging." IEEE Transactions on Biomedical Engineering 68.12 (2021): 3602-3611.

Noble, Jack H et al. "Automatic graph-based localization of cochlear implant electrodes in CT." Medical Image Computing and Computer-Assisted Intervention—MICCAI 2015: 18th International Conference, Munich, Germany, Oct. 5-9, 2015, Proceedings, Part II 18. Springer International Publishing, 2015.

World Health Organization, "Deafness and hearing loss", Apr. 1, 2021, who.int.

World Health Organization, "Ageing and heath", Feb. 5, 2018, who.int.

Lareida, Anita, et al. "High-resolution X-ray tomography of the human inner ear: synchrotron radiation-based study of nerve fibre bundles, membranes and ganglion cells." Journal of microscopy 234.1 (2009): 95-102.

Kaplan W. et al., "Priority Medicines for Europe and the World 2013 Update", Jul. 9, 2013, who.int, URL: https://www.who.int/medicines/areas/priority_medicines/MasterDocJune28_FINAL_Web.pdf, Retrieved from the Internet on Oct. 7, 2024 from the Wayback machine at URL: https://web.archive.org/web/20130717213013/https://www.who.int/medicines/areas/priority_medicines/MasterDocJune28_FINAL_Web.pdf.

Mackay, Crystal, "New tool helps 'tune' cochlear implants to improve hearing", May 27, 2021, Western University News, London, ON, 2021, Retrieved from the Internet on Oct. 7, 2024 from URL: https://news.westernu.ca/2021/05/new-tool-helps-tune-cochlear-implants-improve-hearing/.

Enghag, Sara, et al. "Incus necrosis and blood supply: a micro-CT and synchrotron imaging study." Otology & Neurotology 40.7 (2019): e713-e722.

Iyer, Janani S., et al. "Visualizing the 3D cytoarchitecture of the human cochlea in an intact temporal bone using synchrotron radiation phase contrast imaging." Biomedical Optics Express 9.8 (2018): 3757-3767.

Mei, Xueshuang, et al. "Vascular supply of the human spiral ganglion: novel three-dimensional analysis using synchrotron phase-contrast imaging and histology." Scientific reports 10.1 (2020): 5877.

Rohani, S. Alireza, et al. "Effects of object-to-detector distance and beam energy on synchrotron radiation phase-contrast imaging of implanted cochleae." Journal of Microscopy 273.2 (2019): 127-134.

Rohanii, S. A., et al. "High-resolution imaging of the human incudostapedial joint using synchrotron-radiation phase-contrast imaging." Journal of Microscopy 277.2 (2020): 61-70.

Nordstrom, Charlotta Kämpfe, et al. "A micro-CT and synchrotron imaging study of the human endolymphatic duct with special reference to endolymph outflow and Meniere's disease." Scientific reports 10.1 (2020): 8295.

Nordstrom, Charlotta Kämpfe, et al. "The human endolymphatic sac and inner ear immunity: macrophage interaction and molecular expression." Frontiers in immunology 9 (2019): 3181.

Koch, Robert W. et al., "Measuring Cochlear Duct Length—a historical analysis of methods and results", Journal of Otolaryngology—Head & Neck Surgery, 2017, 46(1): 19. doi: 10.1186/s40463-017-0194-2.

Med El, "Cochlear Implants", medel.com, 2025, Retrieved from URL on May 13, 2025 from URL: https://www.medel.com/en-ca/hearing-solutions/cochlear-implants.

Li, Hao, et al. "Synchrotron radiation-based reconstruction of the human spiral ganglion: implications for cochlear implantation." Ear and hearing 41.1 (2020): 173-181.

Dong, Chao, et al. "Image Super-Resolution Using Deep Convolutional Networks." IEEE Transactions on Pattern Analysis and Machine Intelligence 38.2 (2016): 295-307.

Yang, Jianchao, et al. "Image super-resolution via sparse representation." IEEE transactions on image processing 19.11 (2010): 2861-2873.

Kim, Jiwon et al., "Accurate image super-resolution using very deep convolutional networks." Proceedings of the IEEE conference on computer vision and pattern recognition. 2016.

Lim, Bee, et al. "Enhanced deep residual networks for single image super-resolution." Proceedings of the IEEE conference on computer vision and pattern recognition workshops. 2017.

Wang, Zhihao et al., "Deep learning for image super-resolution: A survey." IEEE transactions on pattern analysis and machine intelligence 43.10 (2020): 3365-3387.

Lightsources, "Canadian Light Source (CLS)", lightsources.org, Jan. 20, 2021, URL: https://lightsources.org/lightsources-of-the-world/americas/canadian-light-source-cls/, Retrieved from the Wayback Machine on Jan. 29, 2026 from URL: https://web.archive.org/web/20210120134411/https://lightsources.org/lightsources-of-the-world/americas/canadian-light-source-cls/.

CBC, "An unprecedented outage: Canadian Light Source synchrotron breakdown cancels research until November", cbc.ca, Jul. 30, 2018, Retrieved from the Internet on Jan. 29, 2026 from URL: https://www.cbc.ca/news/canada/saskatoon/canadian-light-source-synchrotron-1.4767050.

Dong, Chao, et al. "Image Super-Resolution Using Deep Convolutional Networks.", arXiv:1501.00092v3 [cs.CV] Jul. 31, 2015.

* cited by examiner

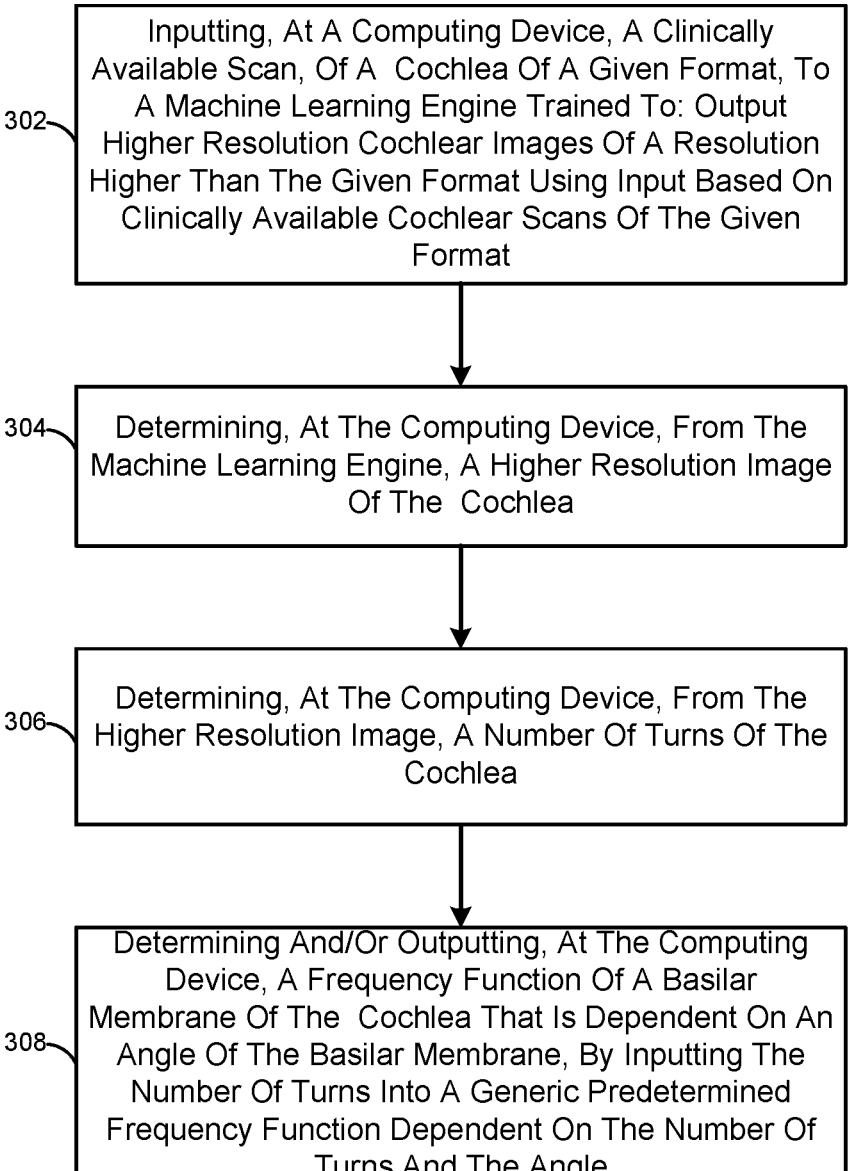

302 — Inputting, At A Computing Device, A Clinically Available Scan, Of A Cochlea Of A Given Format, To A Machine Learning Engine Trained To: Output Higher Resolution Cochlear Images Of A Resolution Higher Than The Given Format Using Input Based On Clinically Available Cochlear Scans Of The Given Format 304 — Determining, At The Computing Device, From The Machine Learning Engine, A Higher Resolution Image Of The Cochlea 306 — Determining, At The Computing Device, From The Higher Resolution Image, A Number Of Turns Of The Cochlea 308 — Determining And/Or Outputting, At The Computing Device, A Frequency Function Of A Basilar Membrane Of The Cochlea That Is Dependent On An Angle Of The Basilar Membrane, By Inputting The Number Of Turns Into A Generic Predetermined Frequency Function Dependent On The Number Of Turns And The Angle

METHOD, DEVICE AND SYSTEM TO DETERMINE A FREQUENCY FUNCTION OF A BASILAR MEMBRANE OF COCHLEAE TO TUNE COCHLEAR IMPLANTS

BACKGROUND

Tuning electrodes of cochlear implants may be based on computer tomography scans, which generally show cochlear bone structure, and assumptions about a position of a basilar membrane relative to the cochlear bone structure. However, such assumptions may be inaccurate, leading to poor tuning of electrodes of cochlear implants.

BRIEF DESCRIPTIONS OF THE DRAWINGS

For a better understanding of the various examples described herein and to show more clearly how they may be carried into effect, reference will now be made, by way of example only, to the accompanying drawings in which:

FIG. 3 depicts a method to determine a frequency function of a basilar membrane of cochleae to tune cochlear implants, according to non-limiting examples.

DETAILED DESCRIPTION

Figure 1:
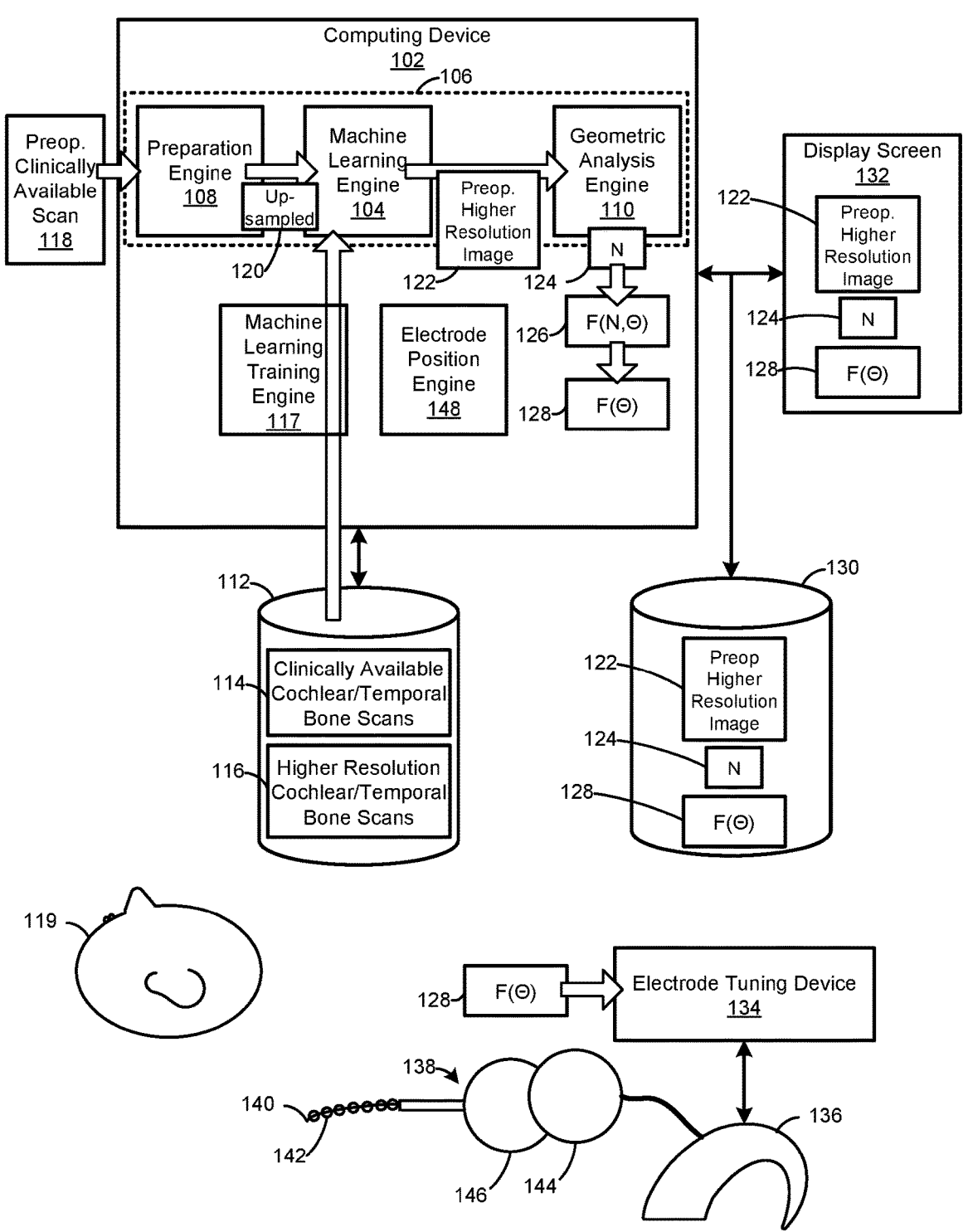
FIG. 1 depicts a system to determine a frequency function of a basilar membrane of cochleae to tune cochlear implants, according to non-limiting examples.

Tuning electrodes of cochlear implants may be based on computer tomography scans, which generally show cochlear bone structure, and assumptions about a position of a basilar membrane relative to the cochlear bone structure. However, such assumptions may be inaccurate, leading to poor tuning of the electrodes of cochlear implants. Such assumptions may include assuming all human cochleae are of one particular shape and/or size and/or measurement of a cochlear duct length along a lateral wall of a cochlea (e.g. which does not exactly correspond to a length of a basilar membrane). However, human cochleae may be of different shapes and sizes, and furthermore basilar membranes are shorter than the cochlear lateral wall length. Hence, a number of turns of human cochleae may vary from person to person, as may a number of turns of a basilar membrane. Similarly, a modiolar axis of a cochlea, a basal plane of a cochlea, a length of a hook of a cochlea, a position of a helicotrema of a cochlea, and the like, may vary from person to person.

In general, a given electrode of an implanted cochlear implant is to stimulate a respective adjacent location of a basilar membrane to cause the basilar membrane to detect (e.g. "hear") a respective frequency, using sounds detected by an external receiver. As such, when a cochlear implant is inserted into a cochlea, assuming all human cochleae are of one particular shape and/or size, may lead to electrodes of the cochlear implant being incorrectly tuned. For example, such assumptions may lead to a determination that an electrode is adjacent to one location, that corresponds to one frequency, of a basilar membrane when the electrode is at another location, that corresponds to another frequency. Such a situation may lead to the basilar membrane being stimulated at the incorrect location and hence the basilar membrane is caused to detect a frequency that may not have been detected by the external receiver. As such, a user of the cochlear implant may hear detected sound inaccurately, which can result in reduced speech understanding, sound quality, and sound localization ability, and/or increased rehabilitation times.

As such, provided herein is a method, device and system to determine a frequency function of a basilar membrane of human cochleae to tune cochlear implants. In particular, a provided device may rely on a machine learning engine that receives a clinically available scan of a human cochlea of a given format, for example as performed on a patient into which a cochlear implant is to be inserted (e.g. a clinically available scan may be performed on the patient prior to an operation to insert a cochlear implant). The machine learning engine outputs a higher resolution image of the human cochlea from which a number of turns of the human cochlea may be determined. The number of turns may be used to determine a frequency function of a basilar membrane of the human cochlea that is dependent on an angle of the basilar membrane, by inputting the number of turns into a generic predetermined frequency function (described in more detail below) dependent on the number of turns and the angle.

Hence, a clinically available scan input to the machine learning engine may be preoperative (e.g. before an operation to insert the cochlear implant occurs). The clinically available scan may undergo some preparation and/or processing prior to being input into the machine learning engine. For example, the machine learning engine may have been trained to receive clinically available scans of a given resolution; hence, the clinically available scan may be converted to the given resolution (e.g. via interpolation techniques when the given resolution is of a higher resolution than a clinically available scan).

From a preoperative clinically available scan, a preoperative higher resolution image of the human cochlea may be determined using the machine learning engine. The preoperative higher resolution image may comprise a preoperative higher resolution segmentation of the human cochlea (e.g. the machine learning engine may have been trained to output segmented higher resolution images that show regions of the human cochlea, and the like). From a preoperative higher resolution image, a number of turns of a human cochlea may be determined more precisely than with preoperative clinically available scans. The preoperative higher resolution image may be further processed, to identify a number of turns of a human cochlea, using geometric analysis (e.g. and/or shape analysis), and which may further include the aforementioned segmentation (e.g. the segmentation may be part of the preoperative higher resolution image received from the machine learning engine and/or segmentation of the image may occur after the preoperative higher resolution image is received from the machine learning engine).

Once the frequency function is determined, and the cochlear implant is inserted into the human cochlea of the patient, a postoperative clinically available scan may occur, and used as input to the machine learning engine, which generates a postoperative higher resolution image of the human cochlea and the cochlear implant, and which further yields angular positions of electrodes of the cochlear implant. The angular positions, which are understood to correspond to angles of the basilar membrane, may be input to the frequency function to determine corresponding frequencies of the electrodes (e.g. a frequency of an electrode comprises a frequency that an adjacent portion of the basilar membrane detects at the angular of the electrode along the basilar membrane).

The frequency function may hence yield the frequencies to which the electrodes of the cochlear implant are to be tuned, and hence may be used to tune the electrodes. Such tuning may include, but is not limited to, providing respective frequencies for the electrodes to an external receiver of the cochlear implant such that the external receiver may provide signals to an internal receiver of the cochlear implant that correspond to the frequencies to control the electrodes to stimulate corresponding positions of the basilar membrane.

Furthermore, the preoperative higher resolution image and the postoperative clinically higher resolution image may be aligned using rigid registration techniques, and the like, and respective angular positions of the electrodes, shown in the postoperative higher resolution image, may be determined from the preoperative higher resolution image. For example, in some instances, the metal of the electrodes may interfere with components of a scanning device (e.g. computerized tomography scanner) that performs the postoperative clinically available scan, and hence the preoperative higher resolution image may be of a better quality than the postoperative higher resolution image determined from the postoperative clinically available scan.

The clinically available scans may comprise helical computerized tomography (CT) scans, cone beam CT scans, and the like. The machine learning engine may be trained from such helical CT scans, cone beam CT scans, and the like, used as training input, and corresponding synchrotron radiation-phase contrast imaging scans and micro-CT scans, and the like, and/or a portion thereof, are used as training output (e.g. and which may be segmented and/or suitable patches of the scans may be identified). Such synchrotron radiation-phase contrast imaging scans and micro-CT scans generally provide a better resolution than helical CT scans, cone beam CT scans, but generally may not be clinically available and/or may be difficult to perform on a live patient. Put another way, helical CT scans and cone beam CT scans may be performed on live patients, but are generally of a poorer quality than synchrotron radiation-phase contrast imaging scans and micro-CT scans; however such synchrotron radiation-phase contrast imaging scans and micro-CT scans may not be performed (and/or may be difficult to perform) on live patients. Hence, by training the machine learning engine using such training input and training output, clinically available scans (e.g. performed on live patients) of human cochlea may be input to the machine learning engine, which outputs higher resolution images of the human cochlea that may be similar in quality to the synchrotron radiation-phase contrast imaging scans and micro-CT scans used to train the machine learning engine.

However, the device and/or the machine learning engine may be further configured to implement similar functionality with clinically available scans of a human temporal bone (e.g. which may include a scan of a human cochlea). For example, such a scan may include, but is not limited to, one or more of a human temporal bone; an external auditory canal; a cochlea; ossicles; a tympanic membrane; an inner ear; a round window; a facial nerve; a chorda tympani nerve; a sigmoid sinus; a carotid artery; a tegmen; and the like. In these examples, the machine learning engine may be trained to receive a preoperative clinically available temporal bone scan and output a preoperative higher resolution image (e.g. which may be segmented to identify the aforementioned anatomical features). As such, a preoperative higher resolution image output by the machine learning engine, from preoperative temporal bone scan, may be used to plan a surgery including, but not limited to, an insertion of a cochlear implant to a cochlea.

An aspect of the specification provides a method comprising: inputting, at a computing device, a clinically available scan, of a cochlea of a given format, to a machine learning engine trained to: output higher resolution cochlear images of a resolution higher than the given format using input based on clinically available cochlear scans of the given format; determining, at the computing device, using the machine learning engine, a higher resolution image of the cochlea; determining, at the computing device, from the higher resolution image, a number of turns of the cochlea; and one or more of determining and outputting, at the computing device, a frequency function of a basilar membrane of the cochlea that is dependent on an angle of the basilar membrane, by inputting the number of turns into a generic predetermined frequency function dependent on the number of turns and the angle.

Another aspect of the specification provides a device comprising: a controller configured to: input a clinically available scan, of a cochlea of a given format, to a machine learning engine trained to: output higher resolution cochlear images of a resolution higher than the given format using input based on clinically available cochlear scans of the given format; determine, using the machine learning engine, a higher resolution image of the cochlea; determine, from the higher resolution image, a number of turns of the cochlea; and one or more of determine, and output, a frequency function of a basilar membrane of the cochlea that is dependent on an angle of the basilar membrane, by inputting the number of turns into a generic predetermined frequency function dependent on the number of turns and the angle.

Attention is directed to FIG. 1 which depicts a system 100 to determine a frequency function of a basilar membrane of cochleae to tune cochlear implants. While devices and techniques are described herein with respect to human cochlea, it is understood that techniques and/or devices provided herein may be more generally applied to other types of cochlea.

The components of the system 100 are generally in communication via communication links which are depicted in FIG. 1, and throughout the present specification, as double-ended arrows between respective components. The communication links includes any suitable combination of wireless and/or wired communication networks and, similarly, the communication links may include any suitable combination of wireless and/or wired links.

Furthermore, flow of data within the system 100 is depicted using single-ended solid arrows, for example to show scans and/or images being provided to components of the system 100.

The system 100 will furthermore be described with respect to engines. As used herein, the term "engine" refers to hardware (e.g., a processor, such as a central processing unit (CPU), graphics processing unit (GPU), an integrated circuit or other circuitry) or a combination of hardware and software (e.g., programming such as machine- or processor-executable instructions, commands, or code such as firmware, a device driver, programming, object code, etc. as stored on hardware). Hardware includes a hardware element with no software elements such as an application specific integrated circuit (ASIC), a Field Programmable Gate Array (FPGA), a PAL (programmable array logic), a PLA (programmable logic array), a PLD (programmable logic device) etc. A combination of hardware and software includes software hosted at hardware (e.g., a software module that is stored at a processor-readable memory such as random access memory (RAM), a hard-disk or solid-state drive, resistive memory, or optical media such as a digital versatile disc (DVD), and/or implemented or interpreted by a processor), or hardware and software hosted at hardware.

The system 100 comprises a computing device 102 implementing one or more machine learning engines 104, for example to implement one or more machine learning algorithms. Furthermore, it is understood that the term "machine learning algorithm", and the like, may be used interchangeably herein with the term "machine learning model".

The machine learning engine 104 may be a component of a machine learning pipeline 106 that further comprises a preparation engine 108 and a geometric analysis engine 110, described in further detail below. In general, the machine learning pipeline 106 may comprise any suitable combination of engines, and the like, that receives a clinically available scan of a cochlea, and outputs a higher resolution scan, as well a number of turns of the cochlea.

As depicted, the system 100 further comprises a memory 112 in the form of a database and external to the computing device 102 and accessible to the computing device 102. However, the memory 112 may be in any suitable format. Furthermore, the memory 112 may include one or more memories, and, in some examples, the memory 112 may be a component of the computing device 102.

As depicted, machine learning training sets, used to train the machine learning engine 104, are stored at the memory 112 in the form of clinically available cochlear scans 114 of a given format (and which, as depicted, may optionally include temporal bone scans of the given format), and corresponding higher resolution cochlear images 116 (and which, as depicted, may optionally include higher resolution temporal bone scans). While the term "higher resolution" is understood to be a relative term, the term "higher resolution" is understood to include the corresponding higher resolution cochlear scans 116 being of a higher resolution than the clinically available cochlear scans 114. Similarly, the corresponding higher resolution cochlear scans 116 may be of a better quality than the clinically available cochlear scans 114; for example, the corresponding higher resolution cochlear scans 116 may more clearly show anatomical features than do the clinically available cochlear scans 114, and/or the corresponding higher resolution cochlear scans 116 may show more anatomical features, and/or finer anatomical features and/or smaller anatomical features than do the clinically available cochlear scans 114.

In particular examples, the clinically available cochlear scans 114 may comprise one or more of helical CT scans, cone beam CT scans, and the like, performed on cadavers (e.g. of humans), and in particular on the cochlear bone (e.g. interchangeably referred to hereafter as the cochlea) of the cadavers. Such clinically available cochlear scans 114 may include scans of the temporal bone of the cadavers, and/or any other portion of the cadavers that includes the cochlea.

Furthermore, the clinically available cochlear scans 114 are understood to show various anatomical features of cochlea, including, but not limited to, a spiral shape thereof, a round window thereof, a hook thereof, a helicotrema thereof, amongst other possibilities, however such features are understood to be shown in a resolution lower than in the corresponding higher resolution cochlear scans 116, which are also understood to show such features.

The corresponding higher resolution cochlear scans 116 may comprise one or more of synchrotron radiation-phase contrast imaging scans and micro-CT scans of the same (and/or similar) portions of the same cadavers on which the clinically available cochlear scans 114 were performed.

In general, synchrotron radiation-phase contrast imaging scans and micro-CT scans are of a higher resolution than the helical CT scans, cone beam CT scans, but the synchrotron radiation-phase contrast imaging scans and micro-CT scans may be difficult to perform on live patients. For example synchrotron radiation-phase contrast imaging scans are acquired using a synchrotron, which relies on radio frequency waves and electro-magnets to accelerate electrons to high speeds and/or high energies, and which produces the radiation for synchrotron radiation-phase contrast imaging; however such radiation may be of a level that is harmful to patients. While micro-CT scans may be performed on live patients, micro-CT scanners generally rely on radiation (e.g. X-rays) at levels that may also be harmful to live patients. Put another way, in some examples, synchrotron radiation-phase contrast imaging scans and/or micro-CT scans may result in destruction and/or degradation of anatomical features being imaged by respective scanners. However, helical CT scans, cone beam CT scans, and the like, may not be harmful (and/or may not be as relatively harmful to live patients) but are of lower resolution than synchrotron radiation-phase contrast imaging scans and micro-CT scans and may not show anatomical features, such as detailed structure of cochleae, as clearly.

Furthermore, while present examples are described with respect to the clinically available cochlear scans 114 comprising helical CT scans and/or cone beam CT scans, and the corresponding higher resolution cochlear scans 116 comprising synchrotron radiation-phase contrast imaging scans and/or micro-CT scans, the scans 114, 116 may be of any suitable format. For example, the clinically available cochlear scans 114 may comprise other types of clinically available scans, such as clinically available magnetic resonance imaging (MRI) scans and the corresponding higher resolution cochlear scans 116 may comprise other types of higher resolution scans including, but not limited to, nano-CT scans.

In general, pairs of scans 114, 116 (e.g. on a same cadaver) are respectively used as training input and training output to the machine learning engine 104.

Furthermore, corresponding higher resolution cochlear scans 116 are described as being scans of a cochlea (e.g. and/or a temporal bone), such corresponding higher resolution cochlear scans 116 used as training output may include portions of such scans and/or label maps of such full scans and/or segmentations of such full scans. For example, the corresponding higher resolution cochlear scans 116 may be segmented prior to being used as training input to the machine learning engine 104 and the segmented portions may be used as the training input rather than the raw data of the corresponding higher resolution cochlear scans 116. For example, the corresponding higher resolution cochlear scans 116 may be analyzed and locations of various anatomical features in the corresponding higher resolution cochlear scans 116 may be identified and labelled, such as the cochlea and/or regions of the cochlea (e.g. edges/ends of the cochlea, the round window, and the like). Such labelling may further include a pitch map of regions of the basilar membrane, and/or regions of the cochlea, that correspond to given frequencies (e.g. a pitch label map).

When the corresponding higher resolution cochlear scans 116 include higher resolution temporal bone scans, such higher resolution temporal bone scans may also be segmented to identify various anatomical features including, but not limited to, one or more of a temporal bone; an external auditory canal; a cochlea; ossicles; a tympanic membrane; an inner ear; a round window; a facial nerve; a chorda tympani nerve; a sigmoid sinus; a carotid artery; a tegmen; and the like.

Hence, higher resolution cochlear scans 116 used as training input, as referred to herein, may comprise, not the raw data of such scans, but portions of the corresponding higher resolution cochlear scans 116 and/or label maps of such scans, and/or identified patches of such scans.

Furthermore, as the corresponding higher resolution cochlear scans 116 (and the like), are generally of a higher resolution than clinically available cochlear scans 114, prior to being used as training input, the clinically available cochlear scans 114 may be upsampled to a resolution of the corresponding higher resolution cochlear scans 116 using any suitable interpolation technique, and the like, including, but not limited to B-spline based interpolations, and the like. Such upsampling may, however, be performed in any suitable manner. Furthermore, such upsampling may be performed by the preparation engine 108, and/or such upsampling may be performed by a machine learning training engine 117, which may convert the scans 114, 116 into formats compatible with the machine learning engine 104 (e.g. depicted the scans 114, 116 are provided to the machine learning engine 104 via the machine learning training engine 117).

The machine learning training engine 117 may further be configured to train the machine learning engine 104 in a training mode, for example using the scans 114,116 and/or as more scans 114, 116 become available.

Furthermore, prior to being used as training sets, the scans 114, 116 may be respectively normalized, for example to account for the scans 114, 116 having been acquired using different scanning devices. Such normalization may include, but is not limited to, applying one or more of artificially noise, blur (e.g. such as Gaussian blur), intensity shifts, interpolations, and the like, to account for different resolutions and/or settings and/or spacings (e.g. between CT slices, and/or different CT slice sizes, and/or different data point spacings) of the different scanning devices.

Hence, in general, the machine learning engine 104 is trained to: output higher resolution cochlear images of a resolution higher than the given format using input based on clinically available cochlear scans of the given format.

Furthermore, the higher resolution cochlear images output by the machine learning engine 104 may be of a same, and/or similar, format as the format of the corresponding higher resolution cochlear scans 116 used to train the machine learning training engine 104. For example, when the corresponding higher resolution cochlear scans 116 are provided in the form of label maps, and/or identified patches and/or segmentations, the higher resolution cochlear images output by the machine learning engine 104 may also be in the form of label maps, and/or identified patches and/or segmentations. Hereafter, for simplicity, such label maps, and/or identified patches and/or segmentations will be generically referred to as segmentations.

An example of operation of the machine learning engine 104 is next described. As depicted, the computing device 102 has received a preoperative clinically available scan 118, for example performed on a live (e.g. human) patient 119 using a same scanning technique used to acquire the clinically available cochlear scans 114. As such, the preoperative clinically available scan 118 is understood to be of a given format, which may be of a same format, and/or a similar format, as the clinically available cochlear scans 114 (e.g. a helical CT scan, a cone beam CT, and the like).

The preoperative clinically available scan 118 of a cochlea may be received via an input device and/or a communication interface of the computing device 102. Put another way, the preoperative clinically available scan 118 may be performed on the patient 119, for example who is to undergo a surgical operation to implant a cochlear implant, and the preoperative clinically available scan 118 may be transferred to, and/or provided to, the computing device 102 in any suitable manner. Such a transfer may be via a computer readable medium (e.g. optical media, a flash drive, and the like) onto which the preoperative clinically available scan 118 has been stored and which is read by an input device of the computing device 102, and/or via an attachment to a message, such as an email, which is received at the computing device 102 via a communication interface of the computing device 102.

As depicted, the computing device 102, inputs the preoperative clinically available scan 118 into the machine learning pipeline 106 by inputting the preoperative clinically available scan 118 into the preparation engine 108, which upsamples the preoperative clinically available scan 118 to produce an upsampled version 120 of the preoperative clinically available scan 118. Hence, in general, the preparation engine 108 is generally configured to convert clinically available scans, such as the clinically available scan 118, into a format suitable for use by the machine learning engine 104. While such conversion may include upsampling (e.g. using B-spline base techniques), the preparation engine 108 may perform any suitable conversion techniques on clinically available scans to convert the clinically available scans into a format used by the machine learning engine 104. In other examples, however, the machine learning engine 104 may be configured to use clinically available scans without any such conversion and/or the machine learning engine 104 may perform such conversions.

As depicted, the machine learning engine 104 receives the upsampled version 120 of the preoperative clinically available scan 118 of the cochlea, and determines a preoperative higher resolution image 122 of the cochlea. Such a determination is based on the training using the scans 114, 116. When the higher resolution scans 116 included the aforementioned segmentation, preoperative higher resolution image 122 also includes such segmentation.

Regardless, it is understood that the preoperative higher resolution image 122 is of a resolution and quality that is higher than, and/or better than, the preoperative clinically available scan 118. For example, the preoperative higher resolution image 122 may be of a similar resolution and/or a similar quality as the corresponding higher resolution cochlear scans 116. As such, the preoperative higher resolution image 122 may show more anatomical features and/or finer anatomical features and/or smaller anatomical features than does the preoperative clinically available scan 118.

As depicted, the higher resolution image 122 is input to the geometric analysis engine 110. The geometric analysis engine 110 is generally configured to perform geometric analysis and/or shape analysis, and the like, on higher resolution images, such as the higher resolution image 122. For example, a cochlea is understood to be generally in a three-dimensional spiral shape, and the geometric analysis engine 110 is generally configured to perform geometric analysis and/or shape analysis on such spiral shapes.

In some examples, the geometric analysis engine 110 may comprise a machine learning engine (and/or machine learning algorithm) trained to perform geometric analysis and/or shape analysis on images of cochlea in higher resolution images generated by the machine learning engine 104, and/or the geometric analysis engine 110 may comprise any suitable algorithm, and/or combinations of algorithms, which perform geometric analysis and/or shape analysis on images of cochlea in higher resolution images generated by the machine learning engine 104.

In particular, however, the geometric analysis engine 110 is generally configured to determine, from the higher resolution image 122 of the cochlea, a number of turns of the cochlea using any suitable geometric analysis and/or shape analysis.

Such determining, from the higher resolution image 122, the number of turns of the cochlea may comprises one or more of: segmenting the higher resolution image 122 (e.g. when not previously segmented via the machine learning engine 104); identifying edges of the cochlea in the higher resolution image 122 (e.g. locations and/or edges of lateral walls and/or hooks and/or bony tips of cochleae, and which may be performed using edge tracing techniques); performing shape analysis on the higher resolution image 122; and performing geometric analysis on the higher resolution image 122.

Such geometric analysis and/or shape analysis may include, but is not limited to, determining, from the higher resolution image 122 of the cochlea, estimations of one or more of: a modiolar axis of the cochlea; a basal plane of the cochlea; a length of a hook of the cochlea; a position of a helicotrema of the cochlea; a respective position of a round window of the cochlea; and/or any other suitable features (e.g. geometric features and/or shape features the cochlea). For example, the modiolar axis and the basal plane may generally represent a spiral shape of a cochlea, while a length of a hook of a cochlea and a position of a helicotrema of a cochlea may represent opposite ends of a cochlea. From such features, a number 124 of turns of the cochlea may be determined.

While the number 124 of turns is represented in FIG. 1 by "N", it is understood that the number of turns may comprise an integer number or a non-integer number. For example, an average number of turns of cochleae may, in general, be around 2.75. However, the number 124 of turns may be any suitable number that is smaller or larger (or equal to) 2.75. Furthermore, the number 124 of turns may be determined as starting from a round window of a cochlea, and/or any other suitable feature of the cochlea that may be identifiable in the preoperative clinically available scan 118 and hence also identifiable in the higher resolution image 122.

While the geometric analysis engine 110 is described as being separate from the machine learning engine 104, in other examples, functionality of the geometric analysis engine 110 may be integrated with the machine learning algorithm, 104.

Furthermore, as the number 124 of turns has been determined from the higher resolution image 122, it is understood that the number 124 of turns may be a more accurate estimation of a number of turns of a cochleae than the average number and/or a number of turns determined from the preoperative clinically available scan 118.

As depicted, the computing device 102 further has access to a generic predetermined frequency function 126 dependent on the number 124 of turns and an angle, Q, of a basilar membrane of a cochlea determined, for example, from a round window of cochlea in which the basilar membrane is located.

For example, the basilar membrane is an anatomical feature located in the cochlear duct of a cochlea that is used by a human body (and the like) to detect sound (e.g. in combination with other anatomical features). The cochlear duct extends from the hook of a cochlea to the helicotrema of a cochlea and hence has a similar spiral shape of the cochlea. As such, the basilar membrane also has a similar spiral shape but extends from a region of a hook of a cochlea, and ends in a region of a helicotrema of a cochlea, though opposite ends of a basilar membrane do not directly correspond with corresponding ends of the cochlear duct. For example, an end of the basilar membrane in a region of the hook does not extend to an end of the hook; similarly, a respective end of the basilar membrane in a region of end of the helicotrema does not extend to a bony tip (e.g. an end of a lateral wall) of the cochlear duct. Hence, assumptions about structure of the cochlea and/or the basilar membrane may lead to inaccurate estimations of a length of the basilar membranes by as much as 2 mm, or more, which further leads to inaccurate estimations of the number of turns of the cochlea and/or a length of the basilar membrane.

The predetermined frequency function 126 is understood to have been determined heuristically from analysis of the corresponding higher resolution cochlear scans 116 (e.g. and hence may be particular to cochlear of humans as the scans 114, 116 are understood to have been performed on cadavers of humans; however, the predetermined frequency function 126 may be determined for any type of cochlea and the scans 114, 116 may be for any type of cadaver that include cochleae). Put another way, the generic predetermined frequency function 126 may be generated from one or more of synchrotron radiation-phase contrast imaging scans and micro-CT scans of a plurality of cochleae and basilar membranes.

In particular examples, the predetermined frequency function 126 has been determined to be:

$$f_{BM} = 2^{\frac{(0.0285N - 0.1978)\theta + 168 + c}{12}} \qquad \text{Equation (1)}$$

At Equation (1), "N" comprises the number 124 of turns, $\theta$ comprises the angle (in degrees) of a basilar membrane as measured from a cochlear round window, and $f_{BM}$ comprises a frequency response of the basilar membrane (e.g. "BM") at the angle. Furthermore, "c" may be determined from:

$$c = -1.26 - 2.33 \cos(0.0059\theta) - 6.84 \sin(0.0059\theta) \qquad \text{Equation (2)}$$

At Equation (2), $\theta$ comprises the angle (in degrees) as in Equation (1).

In particular, the predetermined frequency function 126 may be determined from the corresponding higher resolution cochlear scans 116 which are also understood to show images of basilar membranes of cochlea, and relative locations between ends of the basilar membranes relative to bony structures of respective cochlea, such as hooks and bony tips of cochlear ducts thereof, as well as relative locations between the basilar membranes and round windows of the cochlea. Hence, in general, the predetermined frequency function 126 takes into account the shorter length of the basilar membrane as compared to a length of the cochlear duct.

While the predetermined frequency function 126 of Equation (1) and Equation (2) is understood to be relatively specific, it is further understood that the predetermined frequency function 126 may deviate from Equation (1) and Equation (2) and remain within the scope of present examples. For example, the predetermined frequency function 126 of Equation (1) and Equation (2) has been determined from a given number of synchrotron radiation-phase contrast imaging scans and/or micro-CT scans; hence, as more measurements of basilar membranes using synchrotron radiation-phase contrast imaging scans and micro-CT scans occur, values for the various coefficients and/or numbers of the predetermined frequency function 126 of Equation (1) and Equation (2), and the like, may be determined more precisely. As such, deviations of the various coefficients and/or numbers of the predetermined frequency function 126 of Equation (1) and Equation (2) may be in a given range and remain within the scope of the present specification; for example, such deviations may be in a range of 2%, 5%, and/or up to 10% (and/or any other suitable range), and remain within the scope of the present specification.

Furthermore, while the predetermined frequency function 126 of Equation (1) and Equation (2) is understood to be a function of an angle of a basilar membrane as measured from a round window of a cochlea, the predetermined frequency function 126 of Equation (1) and Equation (2) may be modified to be dependent on the angle of a basilar membrane as measured from any suitable anatomical feature of the cochlea (e.g. and/or the inner ear) that is identifiable in the clinically available cochlear scans 114, and hence also identifiable in the clinically available cochlear scan 118, the corresponding higher resolution cochlear scans 116, and the higher resolution image 122.

Hence, regardless of format, in general, the predetermined frequency function 126 (e.g. represented by Equation (1) and Equation (2)), when modified to input the number 124 of turns of a specific cochlea (e.g. for the patient 119) determined from the preoperative clinically available scan 118, provides a frequency function of a basilar membrane of the specific cochlea.

For example, when the number 124 of turns, "N" has been determined to be 2.73, Equation (1) may be modified to:

$$f_{BM} = 2^{\frac{(0.077805-0.1978)\theta+168+c}{12}} \qquad \text{Equation (3)}$$

For example 0.0285N=0.077805 when N=2.73, and hence, in Equation (3), "0.077805" replaces 0.0285N in Equation (1). However, a specific frequency function may be determined for a specific cochlea using any determined value of the number 124 of turns, "N".

As depicted, the computing device 102 uses the number 124 of turns and the generic predetermined frequency function 126 to generate a frequency function 128 of the basilar membrane of the cochlea that is dependent on the angle, θ, of the basilar membrane. For example, when the number 124 of turns, "N", is 2.73, the frequency function 128 may comprise Equation (3).

In some examples, the frequency function 128 may be used to generate a pitch label map of the cochlea that is generally represented by the frequency function 128. For example, different angular positions (e.g. the angles, θ) of the basilar membrane may be entered into the frequency function 128 to determine pitches (e.g. frequencies) at those positions. Such labelling may be at the preoperative higher resolution image 122 of the cochlea. Such a pitch label map may be used for visualization of frequencies of the basilar membrane.

As depicted, the computing device 102 outputs the frequency function 128, for storage, to a memory 130, which may be a same or different memory as the memory 112. As depicted, the computing device 102 also outputs the number 124 of turns and the preoperative higher resolution image 122 to the memory 130. As depicted, the computing device 102 also outputs the frequency function 128, the number 124 of turns and the preoperative higher resolution image 122 to a display screen 132, for example to control the display screen 132 to render the frequency function 128, the number 124 of turns and the preoperative higher resolution image 122. However, outputting of the frequency function 128, the number 124 of turns and the preoperative higher resolution image 122 may occur in any suitable manner. Furthermore, the computing device 102 may output (e.g. to the display screen 132) a pitch label map of the cochlea represented by the frequency function 128 (e.g. for visualization of frequencies of the basilar membrane of the cochlea), the number 124 of turns and the preoperative higher resolution image 122 (e.g. as an overlay and/or metadata of the preoperative higher resolution image 122).

As will be described in further detail below, the system 100 may also comprise an electrode tuning device 134. While the electrode tuning device 134 is depicted as separate from the computing device 102, in other examples, the computing device 102 may comprise the electrode tuning device 134. Such an electrode tuning device 134 may be used to tune electrodes of a cochlear implant.

For example, as depicted, the electrode tuning device 134 is in communication with an external receiver 136 of a cochlear implant device 138. As depicted, the cochlear implant device 138 comprises a cochlear implant 140 and a plurality of electrodes 142 arranged along a length of the cochlear implant 140. As depicted, the cochlear implant device 138 further comprises an external transmitter 144 and an internal receiver 146. In general, the cochlear implant 140 and the electrodes 142 are understood to be for implantation in a cochlea of a patient, such as the patient 119, and the external receiver 136 may be worn around and/or in an ear, and may receive sounds, which may be converted to corresponding signals which are transmitted, via the external transmitter 144 to the internal receiver 146, which conveys the signals to respective electrodes 142 along the cochlear implant 140 to stimulate adjacent regions of the basilar membrane.

Furthermore, the internal receiver 146 is understood to be for placement under the skin of the patient 119, and the external transmitter 144 may be placed on an external surface of the skin of the patient 119 where the internal receiver 146 is located. As such, tuning of the cochlear implant 140 may occur after implantation of the cochlear implant 140, the electrodes and the internal receiver 146, and after a postoperative clinically available scan of the cochlea of the given format has been acquired and input to the machine learning engine 104 (e.g. similar to as described above with respect to the preoperative clinically available scan 118), the postoperative clinically available scan including an image of the cochlear implant 140 inserted into a cochlea.

The machine learning engine 104 outputs a postoperative higher resolution image of the cochlea and the cochlear implant 140 from which angular positions of the electrodes 142 may be determined, and input to the frequency function represented by Equation (3) (e.g. and Equation (2)). Hence, the frequency function represented by Equation (3) and Equation (2) may be used to determine which frequencies respective electrodes 142 of the cochlear implant 140 correspond to, and such frequencies may be provided by the electrode tuning device 134 to the external receiver 136, which may use such frequencies to generate respective signals for the electrodes 142. Such examples are described in more detail below with respect to FIG. 4. Furthermore, as depicted, functionality for determining electrode positions may be provided via an electrode position engine 148, described in more detail below.

Furthermore, as depicted the frequency function 128 may be provided to the electrode tuning device 134 via optical media, a message attachment and the like. Alternatively, the frequency function 128 may be retrieved from the memory 130 by the electrode tuning device 134. Regardless it is understood that the electrode tuning device 134 may have access to the frequency function 128. In such examples, angular positions of the electrodes 142 in a cochlea are provided to the electrode tuning device 134, which used the frequency function 128 and the electrode positions to determine their respective frequencies. Alternatively, the respective frequencies may be determined at the computing device 102 (e.g. by the electrode position engine 148) and provided to the electrode tuning device 134.

Figure 2:
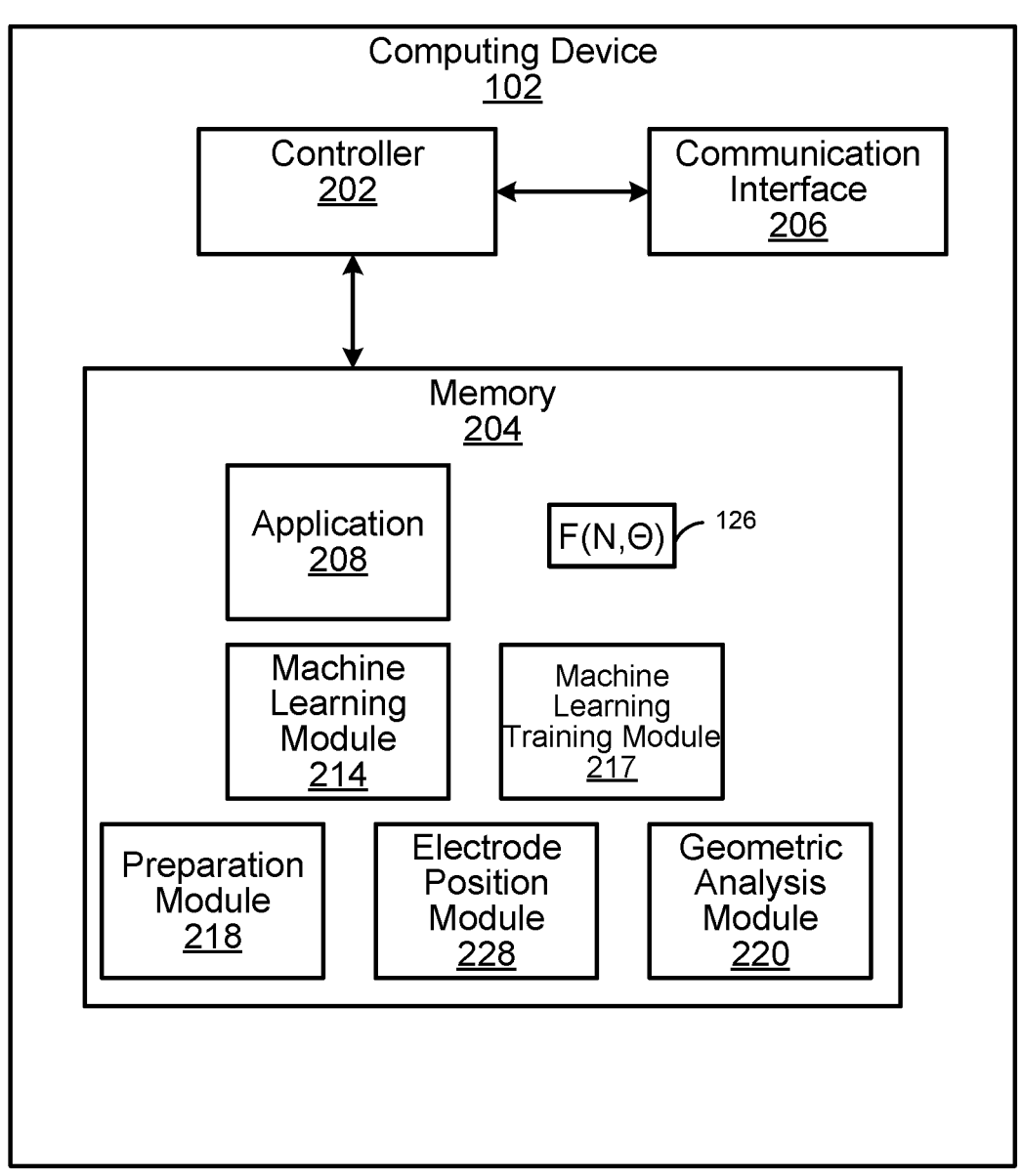
FIG. 2 depicts a device used to determine a frequency function of a basilar membrane of cochleae to tune cochlear implants, according to non-limiting examples.

Attention is next directed to FIG. 2 which depicts a block diagram of an example of the computing device 102 that includes a controller 202 communicatively coupled to a memory 204 and a communication interface 206. It is furthermore understood that the computing device 102 may be implemented as a personal computer, a laptop computer, one or more servers and/or one or more cloud computing devices; furthermore, functionality of the computing device 102 may be distributed across one or more servers and/or one or more cloud computing devices, and the like.

The controller 202 comprise one or more general-purpose processors and/or one or more special purpose logic devices, such as microprocessors (e.g., a central processing unit, a graphics processing unit, etc.), a digital signal processor, a microcontroller, an ASIC, an FPGA, a PAL, a PLA, a PLD (programmable logic device), etc.

The controller 202 is interconnected with the memory 204 which may comprise any suitable memory that stores instructions, for example, as depicted, in the form of applications and/or modules that, when implemented by the controller 202, cause the controller 202 to implement the functionality described herein including, but not limited to the machine learning engine 104 and/or a machine learning engine. The memory 204 may be implemented as a suitable non-transitory computer-readable medium (e.g. a suitable combination of non-volatile and volatile memory subsystems including any one or more of Random Access Memory (RAM), read only memory (ROM), Electrically Erasable Programmable Read Only Memory (EEPROM), flash memory, magnetic computer storage, and the like). The controller 202 and the memory 204 may be generally comprised of one or more integrated circuits (ICs).

The controller 202 is also interconnected with a communication interface 206, which generally enables the computing device 102 to communicate with the other components of the system 100 via one or more communication links. The communication interface 206 therefore includes any necessary components (e.g. network interface controllers (NICs), radio units, and the like) to communicate with the other components of the system 100 via one or more communication links (e.g. via one or more communication networks). The specific components of the communication interface 206 may be selected based on upon types of the communication links. The computing device 102 may also include input and output devices connected to the controller 202, such as keyboards, pointing devices, display screens, computer-readable medium reading devices (e.g. an optical media reader, a flash memory port) and the like (not shown).

The memory 204 includes an application and modules. As used herein, an "application" and/or a "module" (in some examples referred to as a "software module") is a set of instructions that when implemented or interpreted by a controller and/or a processor, or stored at a processor-readable medium realizes a component or performs a method and/or is used to implement one or more of the engines 104, 108, 110, 117, 148, and the like.

As depicted, the memory 204 stores an application 208, which corresponds to functionality described below with respect to blocks of a method 300 of FIG. 3, and modules 214, 217, 218, 220, 228 which correspond to functionality of the engines 104, 108, 110, 117, 148. For example, the machine learning module 214, when processed by the controller 202, causes the controller 202 to implement the machine learning engine 104. Similarly, the preparation module 218, when processed by the controller 202, causes the controller 202 to implement the preparation engine 108. Similarly, the geometric analysis module 220, when processed by the controller 202, causes the controller 202 to implement the geometric analysis engine 110. Similarly, the machine learning training module 217, when processed by the controller 202, causes the controller 202 to implement the machine learning training engine 117. Similarly, the electrode position module 228, when processed by the controller 202, causes the controller 202 to implement the electrode position engine 148.

In general, the application 208, when implemented by the controller 202, may be configured to control interactions between the engines 104, 108, 110, 117, 148, for example to control the machine learning pipeline 106, and/or provide any other suitable functionality as described herein, for example as described below with respect to the method of FIG. 3.

Attention is now directed to FIG. 3 which depicts a flowchart representative of a method 300 to determine a frequency function of a basilar membrane of cochleae to tune cochlear implants. The operations of the method 300 of FIG. 3 correspond to machine readable instructions that are executed by the computing device 102 (e.g. and/or by one or more cloud computing devices), and specifically the controller 202 of the computing device 102. In the illustrated example, the instructions represented by the blocks of FIG. 3 may be stored at the memory 204 for example, at least in part as the application 208 and/or the modules 214, 218, 220, 228. In some examples, the controller 202 implementing the application 208 may, in conjunction, implement one or more the engines 104, 108, 110, 148 corresponding to the modules 214, 218, 220, 228. The method 300 of FIG. 3 is one way in which the computing device 102, and/or the controller 202 and/or the system 100 may be configured. However, while the method 300 is specifically described with regards to being implemented by the controller 202 and/or the computing device 102, it is understood that the method 300 may be implemented by one or more computing devices, one or more servers, one or more cloud computing devices, and/or one or more controllers thereof.

Furthermore, the following discussion of the method 300 of FIG. 3 will lead to a further understanding of the system 100, and its various components.

The method 300 of FIG. 3 need not be performed in the exact sequence as shown and likewise various blocks may be performed in parallel rather than in sequence. Accordingly, the elements of method 300 are referred to herein as "blocks" rather than "steps." The method 300 of FIG. 3 may be implemented on variations of the system 100 of FIG. 1, as well.

Furthermore, while the method 300 is described with respect to using the preoperative clinically available scan 118, it is understood that, in some examples, a postoperative clinically available scan may be used with the method 300 (e.g. a clinically available scan that occurs after implantation of a cochlear implant). While electrodes of cochlear implants of postoperative clinically available scan may cause interference, which may lead to postoperative clinically available scans being of a poorer quality, and/or to include more noise, than preoperative clinically available scans, in some examples, suitable image filtering techniques may be used on postoperative clinically available scans to improve the quality and/or filter such noise and render such postoperative clinically available scans suitable for used with the method 300.

At a block 302, the controller 202 and/or the computing device 102, inputs the clinically available scan 118 of a cochlea of a given format, to the machine learning engine 104. The machine learning engine 104 is generally understood to be trained to: output higher resolution cochlear images of a resolution higher than the given format using input based on clinically available cochlear scans of the given format.

Examples of such inputting are described with reference to FIG. 1. Hence, as previously described, it is understood that, in some examples, inputting the clinically available scan 118 of the cochlea to the machine learning engine 104 may comprise the controller 202 and/or the computing device 102, prior to the inputting: generating the upsampled version 120 of the clinically available scan 118, the upsampled version 120 of the clinically available scan 118 used as input to the machine learning engine 104, and the upsampled version 120 having a same resolution as one or more of the higher resolution image 122 and the corresponding higher resolution cochlear scans 116 used to train the machine learning engine 104.

At a block 304, the controller 202 and/or the computing device 102 determines, using the machine learning engine 104, the higher resolution image 122 of the cochlea. Examples of such determinations are described with reference to FIG. 1. However, it is understood that the higher resolution image 122 may comprise a higher resolution segmentation of the cochlea represented by the clinically available scan 118.

For example, as has already been described, the clinically available scan 118 may comprise a preoperative clinically available scan, and the higher resolution image may similarly comprise a preoperative higher resolution image, and which may further comprise a higher resolution segmentation of the cochlea represented by the clinically available scan 118.

At a block 306, the controller 202 and/or the computing device 102 determines, from the higher resolution image 122, the number 124 of turns of the cochlea, as also described above with respect to FIG. 1.

As has also already been described, at the block 306, the controller 202 and/or the computing device 102 may determine, from the higher resolution image 122, the number 124 of turns of the cochlea by one or more of: segmenting the higher resolution image 122; identifying edges of the cochlea in the higher resolution image 122; performing shape analysis on the higher resolution image 122; performing geometric analysis on the higher resolution image 122; and the like.

Similarly, as has already been described, at the block 306, the controller 202 and/or the computing device 102 may determine, from the higher resolution image 122, the number 124 of turns of the cochlea by analyzing the higher resolution image 122 to determine estimations of one or more of: a modiolar axis of the cochlea; a basal plane of the cochlea; a length of a hook of the cochlea; a position of a helicotrema of the cochlea; and the like.

At a block 308, the controller 202 and/or the computing device 102 determines, and/or outputs (e.g. one or more of determines and outputs), the frequency function 128 of a basilar membrane of the cochlea that is dependent on an angle of the basilar membrane, by inputting the number 124 of turns into the generic predetermined frequency function 126 dependent on the number 124 of turns and the angle. Such determination and outputting has also been previously described with respect to FIG. 1.

The method 300 may include other aspects. For example, at the block 308, the aforementioned frequency label map may be determined and/or outputted.

Furthermore, the method 300 may further include the controller 202 and/or the computing device 102 training the machine learning engine in a training mode. For example, in such a training mode (e.g. implemented via the machine learning training engine 117), the controller 202 and/or the computing device 102 may use, as training input to the machine learning engine 104, one or more of the clinically available cochlear scans 114 of the given format and upsampled versions of the clinically available cochlear scans 114. The given format may comprise one or more of helical CT scans, cone beam CT scans, and the like.

Furthermore, in such a training mode (e.g. implemented via the machine learning training engine 117), the controller 202 and/or the computing device 102 may use, as training output, corresponding higher resolution cochlear scans 116. The corresponding higher resolution cochlear scans 116 may comprise one or more of corresponding higher resolution cochlear images and corresponding higher resolution cochlear segmentations. The corresponding higher resolution cochlear scans 116 may be based on one or more of synchrotron radiation-phase contrast imaging scans and micro-CT scans. Furthermore, when upsampled versions of the clinically available cochlear scans 114 are used as training input, upsampled versions of the clinically available cochlear scans 114 are understood to have a same resolution as the corresponding higher resolution cochlear scans 116.

Furthermore, the clinically available scan 118 may comprise a preoperative clinically available scan for planning insertion of a cochlear implant into a cochlea. Hence, the higher resolution image 122 may comprise one or more of a preoperative higher resolution image and a preoperative higher resolution segmentation, which may also be used for planning insertion of a cochlear implant into a cochlea. In particular, a preoperative clinically available scan, a preoperative higher resolution image, and a preoperative higher resolution segmentation, as describe herein, may be of one more of: a temporal bone; an external auditory canal; ossicles; a tympanic membrane; an inner ear; a round window; a facial nerve; a chorda tympani nerve; a sigmoid sinus; a carotid artery; a tegmen; and/or any other suitable anatomical feature. In these examples, the higher resolution image 122 may be rendered at the display screen 132, and/or at a display screen of any suitable device, and used to plan insertion of the cochlear implant 140 into a cochlea of a patient (e.g. as well as insertion of the internal receiver 146 under skin of the patient), such as the patient 119.

In some examples, when the higher resolution image 122 includes the temporal bone, and the like, the higher resolution image 122 may be input to a surgical planning computing device (which may include, but is not limited to, the computing device 102) configured to plan surgeries. Such a surgical planning computing device may use the higher resolution image 122 to plan a path for insertion of the cochlear implant 140 into a cochlea by a surgeon.

Similarly, in some examples, when the higher resolution image 122 includes the temporal bone, and the like, the higher resolution image 122 may be input to a robotic surgical system which uses one or more robotic arms to perform surgeries. Such a robotic surgical system may use the higher resolution image 122 to plan a path for insertion of the cochlear implant 140 into a cochlea by the one or more robotic arms.

Such surgical planning may further include selection of a suitable cochlear implant for a particular patient, such as the patient 119. For example, the higher resolution image 122 may indicate a length of a cochlear duct, and a cochlear implant of a similar length may be selected, and/or manufactured accordingly. However, techniques described herein may generally be implemented using off-the-shelf cochlear implants.

In examples where the clinically available scan 118, used at the block 302, comprises a preoperative clinically available scan, and the higher resolution image 122 determined at the block 304 comprises a preoperative higher resolution image, the method 300 may further comprise (e.g. see FIG. 4) the controller 202 and/or the computing device 102 inputting a postoperative clinically available scan of the cochlea (e.g. represented by the clinically available scan 118) of the given format to the machine learning engine 104, the postoperative clinically available scan including an image of the cochlear implant 140 inserted into the cochlea; determining, using the machine learning engine 104, a postoperative higher resolution image of the cochlea and the cochlear implant 140; determining, from the postoperative higher resolution image, respective positions (e.g. angular positions) of the electrodes 142 of the cochlear implant; and tuning the electrodes 142 of the cochlear implant 140 based on the respective positions of the electrodes 142 and the frequency function 128. For example, respective angular positions of the electrodes 142 may be input to the frequency function 128 and provided to the external receiver 136 via the electrode tuning device 134, as described herein.

In some of these examples, as postoperative clinically available scans that include electrodes of cochlear implants may be of a poorer quality than preoperative clinically available scans (for example due to interference of electrodes with scanning devices), the method 300 may further comprise the controller 202 and/or the computing device 102: aligning the postoperative higher resolution image with the preoperative higher resolution image 122; and determining the respective positions of the electrodes 142 of the cochlear implant 140 at the preoperative higher resolution image 122. Such alignment may occur using rigid registration techniques and/or any other suitable techniques, and positions of the electrodes 142 at the preoperative higher resolution image 122 may be more precisely determined, for example relative to a round window of the cochlea, than with the postoperative higher resolution image due to better quality of the preoperative higher resolution image 122 as compared to the postoperative higher resolution image.

Furthermore, such functionality for determining electrode position may be implemented via the electrode position engine 148.

In other examples, however, electrode positions may be determined from the postoperative higher resolution image. Indeed, in yet further examples, the method 300 may be implemented using the postoperative higher resolution image, presuming the postoperative higher resolution image and/or the postoperative clinically available scan is of a suitable quality.

Figure 4:
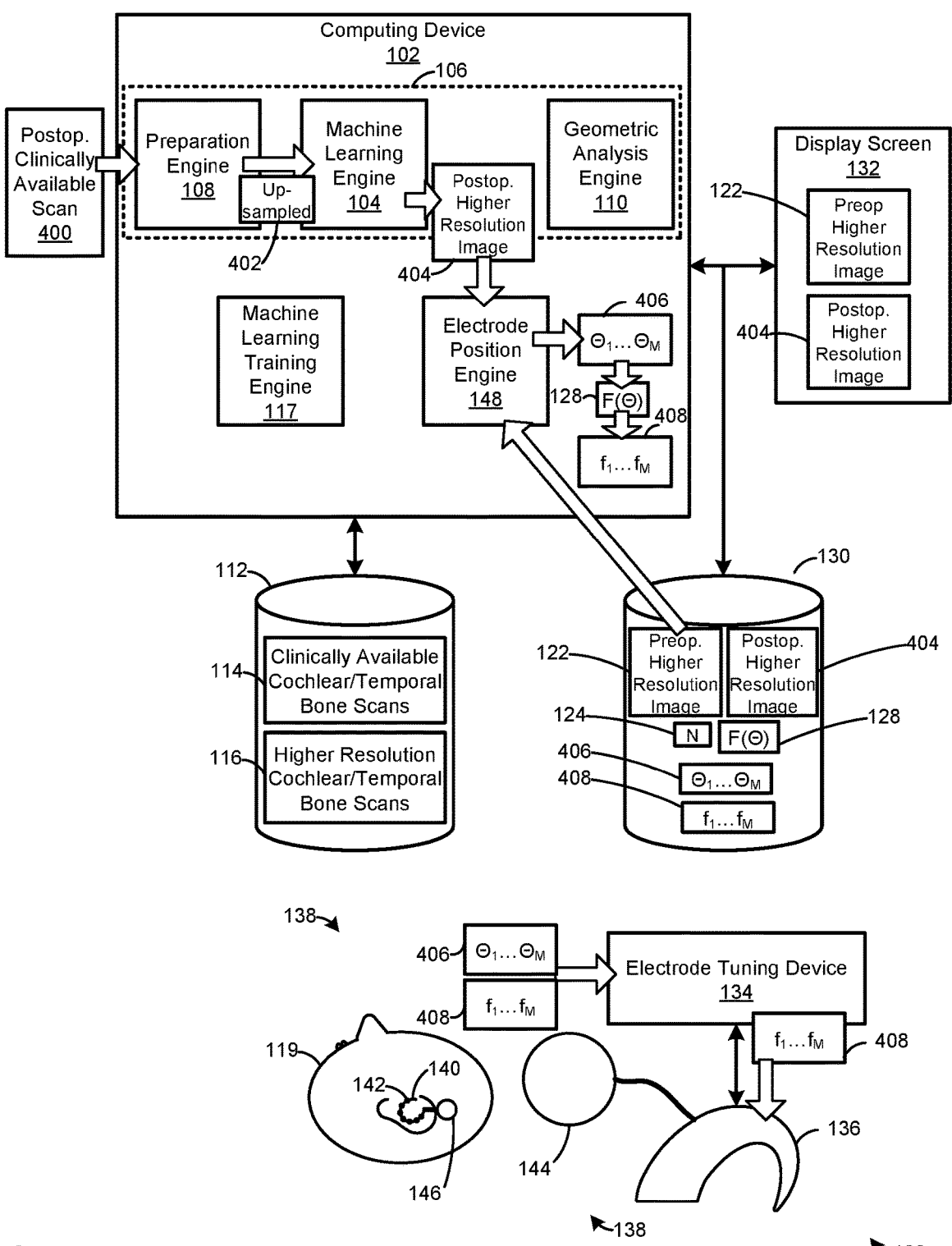
FIG. 4 depicts the system of FIG. 1 determining angular positions of electrodes of a cochlear implant, according to non-limiting examples.

Examples of determining electrode positions of a cochlear implant are next described with respect to FIG. 4, which is substantially similar to FIG. 1, with like components having like numbers. However, in FIG. 4, the cochlear implant 140 is understood to have been implanted in a cochlea (not depicted) of the patient 119; the internal receiver 146 is also understood to have been implanted under skin of the patient 119. It is further understood in FIG. 4 that the cochlear implant 140 etc., and/or other components of the cochlear implant device 138 are not drawn to size.

Furthermore, as depicted in FIG. 4, a postoperative clinically available scan 400 has been performed on the patient 119, for example to scan their cochlea and the implanted cochlear implant 140. The postoperative clinically available scan 400 is input to the machine learning pipeline 106, and the preparation engine 108 determines an upsampled version 402 of the postoperative clinically available scan 400. The upsampled version 402 is input to the machine learning engine 104, which determines a postoperative higher resolution image 404 of the cochlea and the cochlear implant 140. Hence, determination of the postoperative higher resolution image 404 occurs in a similar manner as determination of the preoperative higher resolution image 122.

While geometric analysis may occur on the postoperative higher resolution image 404, as depicted and in contrast to FIG. 1, the postoperative higher resolution image 404 is provided to the electrode position engine 148 (e.g. rather than the geometric analysis engine 110). Furthermore, the preoperative higher resolution image 122 is retrieved from the memory 130, along with the frequency function 128 which are understood to be specific to the patient 119. The preoperative higher resolution image 122 is also provided to the electrode position engine 148 which may align the images 122, 404 (e.g. using rigid registration techniques, and the like) to determine angular positions 406, $\Theta_1 \ldots \Theta_M$, of the electrodes 142. In particular, the electrode position engine 148 may align the images 122, 404 such that images of the electrodes 142 in the postoperative higher resolution image 404 are shown relative to the preoperative higher resolution image 122. A position of the round window of the cochlea of the patient 119 shown in the preoperative higher resolution image 122 may also be determined by the electrode position engine 148 and/or such a position may have already been labelled in the preoperative higher resolution image 122. Regardless, the electrode position engine 148 determines the angular positions 406 of the electrodes 142 as measured from the position of the round window of the cochlea of the patient 119.

As depicted, there are an integer number "M" of the angular positions 406, $\Theta_1 \ldots \Theta_M$, which may correspond on a one-to-on basis with the number of electrodes 142 (e.g. in these examples is an "M" number of the electrodes 142). Furthermore, the first angular position 406, $\Theta_1$, is understood to comprise an angular position of the electrode 142 closest to the round window of the cochlea of the patient 119, as identified in one or more of the images 122, 404; and the last angular position 406, $\Theta_M$, is understood to comprise an angular position of the electrode 142 furthest from the round window of the cochlea of the patient 119 (e.g. closest to the bony tip of the cochlea). Other angular positions 406 are understood to correspond, one-to-one, with the other electrodes 142 between the first electrode 142 and the last electrode 142.

As depicted, the computing device 102 (e.g. via execution of the application 208) inputs each angular position 406 to the frequency function 128 to respectively determine frequencies 408, $f_1 \ldots f_M$, that correspond to positions on a basilar membrane that are adjacent to the electrodes 142, at the angular positions 406. Alternatively, the electrode position engine 148 may perform such functionality.

Alternatively, the electrode tuning device 134 (e.g. when separate from the computing device 102) may perform such functionality, presuming the electrode tuning device 134 has received the frequency function 128 as depicted in FIG. 1. As such, as depicted, the angular positions 406 may be provided to the electrode tuning device 134 (e.g. via an input device reading a computer readable memory on which the angular positions 406 are provided, a message attachment that includes the angular positions 406, and the like).

Alternatively, as also depicted, the frequencies 408 may be provided to the electrode tuning device 134.

Alternatively, as also depicted, the angular positions 406 and/or the frequencies 408 may be stored at the memory 130 (e.g. by the computing device 102), and the electrode tuning device 134 may retrieve the angular positions 406 and/or the frequencies 408 from the memory 130.

Indeed, as depicted, the computing device 102 may store the angular positions 406 and/or the frequencies 408 at the memory 130, as well as the postoperative higher resolution image 404, in association with the number 124, and the frequency function 128. While not depicted, the scans 118, 400 may also be stored at the memory 130.

Regardless, the electrode tuning device 134 is understood to receive and/or determine and/or has access to the frequencies 408, which are provided to the external receiver 136 of the cochlear implant device 138 to tune the electrodes 142. In particular, the external receiver 136 may process sounds detected by the external receiver 136 to produce respective signals corresponding to the frequencies 408 of the detected sounds, and the respective signals may be used to control the respective electrodes 142 to stimulate respective adjacent locations of a basilar membrane of the cochlea of the patient 119, which are understood to correspond to the frequencies 408.

Figure 5:
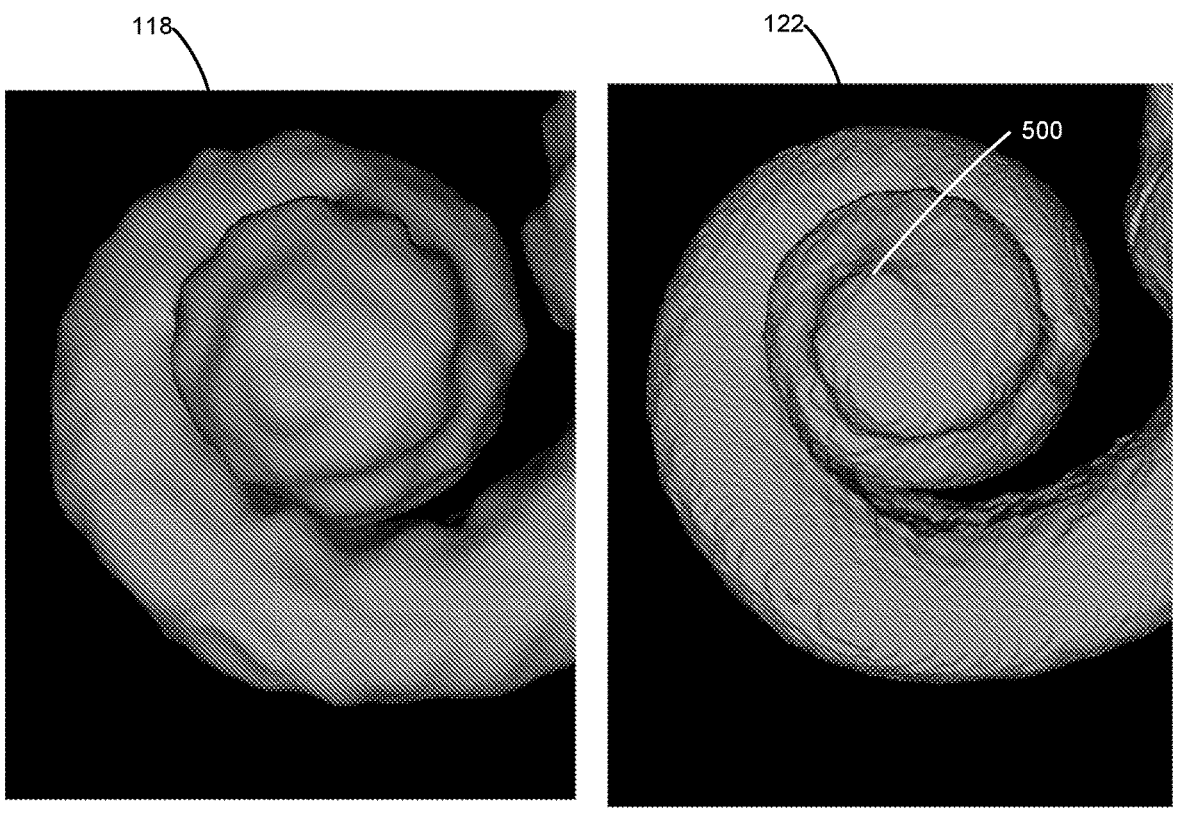
FIG. 5 depicts a clinically available scan of a cochlea, and a higher resolution image thereof generated using a machine learning engine, according to non-limiting examples.

Attention is next directed to FIG. 5 which depicts examples of the preoperative clinically available scan 118 of a cochlea, as generated by a scanning device, and the preoperative higher resolution image 122 of the cochlea, as generated by the machine learning engine 104. While, both the clinically available scan 118 and the higher resolution image 122 show spiral shape of the cochlea, it is apparent, by comparing the clinically available scan 118 to the higher resolution image 122, that the higher resolution image 122 is of a better quality than the clinically available scan 118 and shows more detail of the cochlea. For example, a helicotrema 500 of the depicted cochlea, and/or an end that corresponds to the bony tip of the cochlear duct, is clearly shown in the higher resolution image 122 but not the clinically available scan 118.

Furthermore, from the example clinically available scan 118 and the example higher resolution image 122 of FIG. 5, it is apparent that both the clinically available scan 118 and the higher resolution image 122 show external views of the cochlea and further are three-dimensional. While not depicted, it is understood that both the clinically available scan 118 and the higher resolution image 122 further include three-dimensional internal structures of the cochlea, and hence may be processed to show such internal structures and/or to show slices of the higher resolution image 122.

Figure 6:
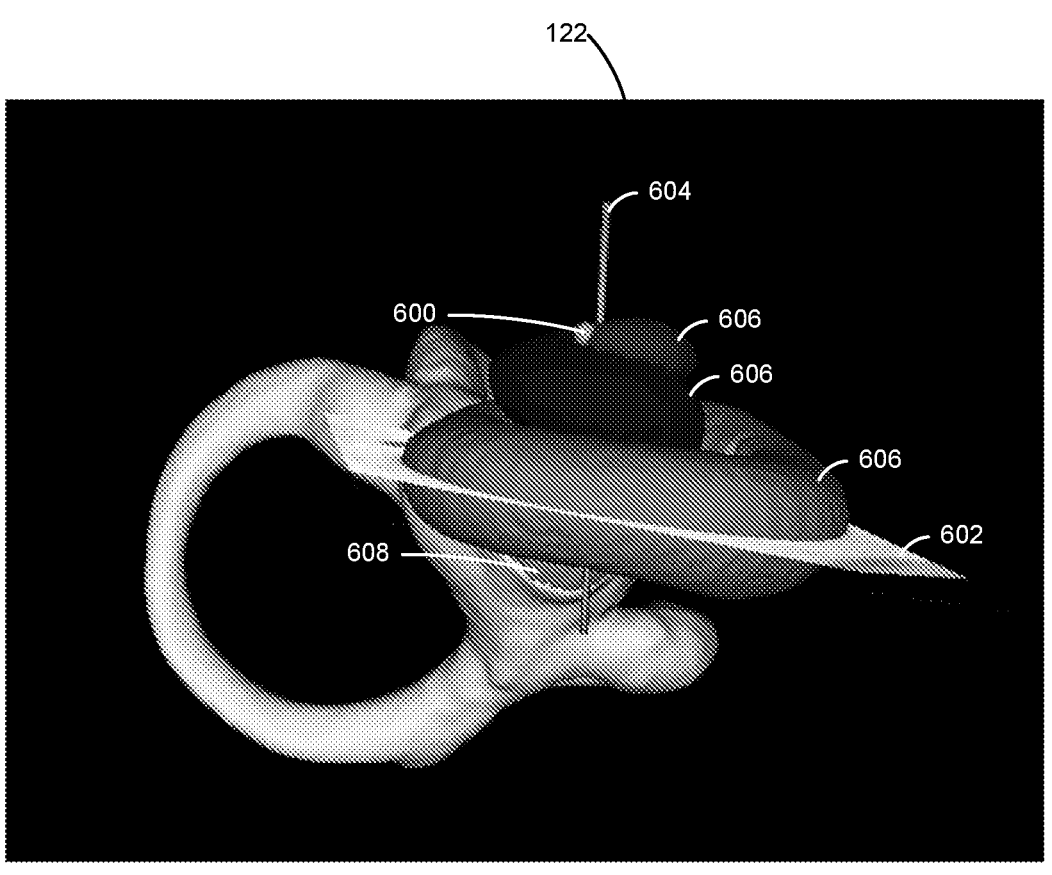
FIG. 6 depicts geometric analysis of a higher resolution image of a cochlea, according to non-limiting examples.

Attention is next directed to FIG. 6 which depicts an example of geometric analysis of another example higher resolution image 122 (e.g. as performed by the geometric analysis engine 110). As depicted, the example higher resolution image 122, which also clearly shows an external three-dimensional view of a cochlea, has been analyzed to determine a helicotrema 600 of the depicted cochlea (and/or an end that corresponds to the bony tip of the cochlear duct), a basal plane 602 of the depicted cochlea, a modiolar axis 604 of the depicted cochlea, various segments 606 of a spiral of the depicted cochlea, a hook 608 of the depicted cochlea, and the like, The positions of such features may be used by the geometric analysis engine 110 to determine the number 124 of turns of the depicted cochlea.

Figure 7:
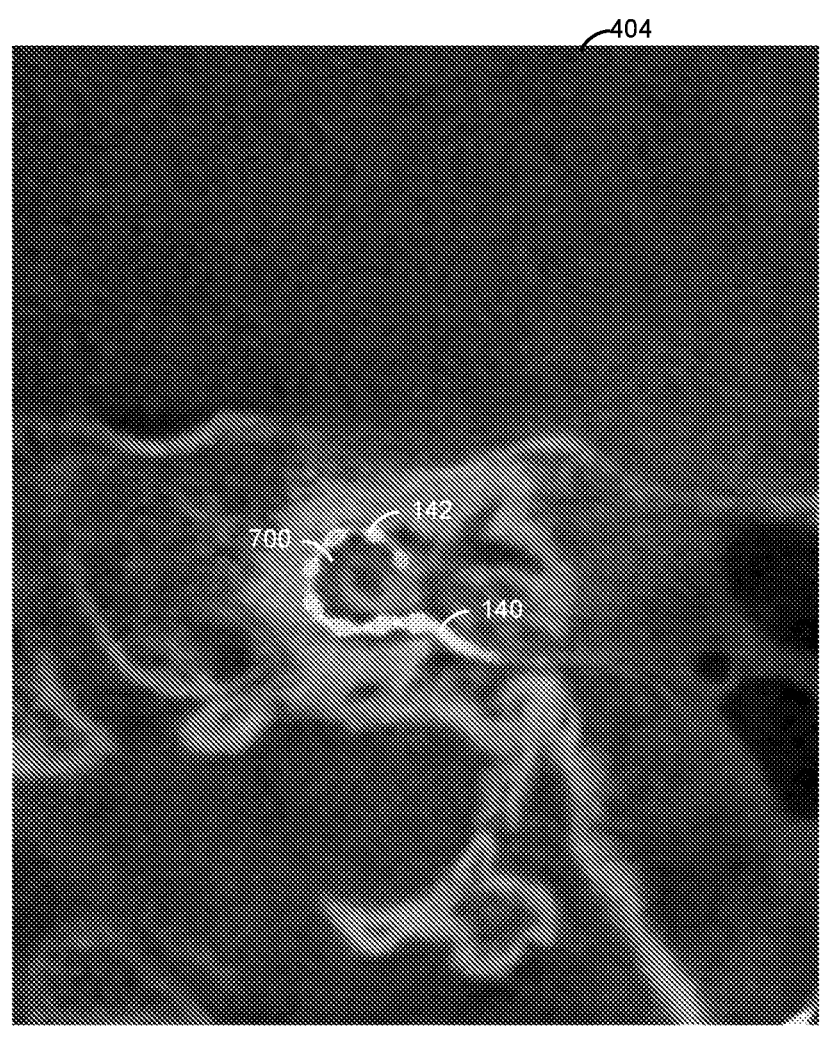
FIG. 7 depicts a slice of a higher resolution image of a cochlea with a cochlear implant, according to non-limiting examples.

Attention is next directed to FIG. 7 which depicts an example of the postoperative high resolution image 404 and, in particular, a view of a slice of the postoperative high resolution image 404 that includes the electrodes 142 of the cochlear implant 140 as implanted in a cochlear duct 700. From the postoperative high resolution image 404, for example as aligned with the preoperative higher resolution image 122, the angular positions 406 of the respective electrodes 142 may be determined and used as input to the frequency function 128.

As should by now be apparent, the operations and functions of the devices described herein are sufficiently complex as to require their implementation on a computer system, and cannot be performed, as a practical matter, in the human mind. In particular, computing devices, and the lie, such as set forth herein are understood as requiring and providing speed and accuracy and complexity management that are not obtainable by human mental steps, in addition to the inherently digital nature of such operations. For example, a human mind cannot interface directly with, RAM or other digital storage, cannot convert scans to images as described herein, among other features and functions set forth herein).

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, XZ, and the like). Similar logic can be applied for two or more items in any occurrence of "at least one . . . " and "one or more . . . " language.

The terms "about", "substantially", "essentially", "approximately", and the like, are defined as being "close to", for example as understood by persons of skill in the art. In some examples, the terms are understood to be "within 10%," in other examples, "within 5%", in yet further examples, "within 1%", and in yet further examples "within 0.5%".

Persons skilled in the art will appreciate that in some examples, the functionality of devices and/or methods and/or processes described herein can be implemented using pre-programmed hardware or firmware elements (e.g., application specific integrated circuits (ASICs), electrically erasable programmable read-only memories (EEPROMs), etc.), or other related components. In other examples, the functionality of the devices and/or methods and/or processes described herein can be achieved using a computing apparatus that has access to a code memory (not shown) which stores computer-readable program code for operation of the computing apparatus. The computer-readable program code could be stored on a computer readable storage medium, which is fixed, tangible and readable directly by these components, (e.g., removable diskette, CD-ROM, ROM, fixed disk, USB drive). Furthermore, it is appreciated that the computer-readable program can be stored as a computer program product comprising a computer usable medium. Further, a persistent storage device can comprise the computer readable program code. It is yet further appreciated that the computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

Persons skilled in the art will appreciate that there are yet more alternative examples and modifications possible, and that the above examples are only illustrations of one or more examples. The scope, therefore, is only to be limited by the claims appended hereto.

What is claimed is:

1. A method comprising:

inputting, at a computing device, a clinically available scan, of a cochlea of a given format, to a machine learning engine trained to: output higher resolution cochlear images of a resolution higher than the given format using input based on clinically available cochlear scans of the given format;

determining, at the computing device, using the machine learning engine, a higher resolution image of the cochlea;

determining, at the computing device, from the higher resolution image, a number of turns of the cochlea; and one or more of determining and outputting, at the computing device, a frequency function of a basilar membrane of the cochlea that is dependent on an angle of the basilar membrane, by inputting the number of turns into a generic predetermined frequency function dependent on the number of turns and the angle.

2. The method of claim 1, wherein the clinically available scan comprises a preoperative clinically available scan, and the higher resolution image comprises a preoperative higher resolution image, the method further comprising:

inputting, at the computing device, a postoperative clinically available scan of the cochlea of the given format to the machine learning engine, the postoperative clinically available scan including an image of a cochlear implant inserted into the cochlea;

determining, at the computing device, using the machine learning engine, a postoperative higher resolution image of the cochlea and the cochlear implant;

determining, at the computing device, from the postoperative higher resolution image, respective positions of electrodes of the cochlear implant; and tuning the electrodes of the cochlear implant based on the respective positions of the electrodes and the frequency function.

3. The method of claim 2, wherein determining, at the computing device, the respective positions of the electrodes of the cochlear implant comprises:

aligning the postoperative clinically available scan with the preoperative higher resolution image; and determining the respective positions of the electrodes of the cochlear implant at the preoperative higher resolution image.

4. The method of claim 1, further comprising training the machine learning engine in a training mode using:

as training input to the machine learning engine, one or more of the clinically available cochlear scans of the given format and upsampled versions of the clinically available cochlear scans; wherein the given format comprises one or more of helical computerized tomography (CT) scans and cone beam CT scans; and as training output to the machine learning engine, corresponding higher resolution cochlear scans, the corresponding higher resolution cochlear scans comprising one or more of corresponding higher resolution cochlear images and corresponding higher resolution cochlear segmentations, the corresponding higher resolution cochlear scans based on one or more of synchrotron radiation-phase contrast imaging scans and micro-CT scans; wherein the upsampled versions of the clinically available cochlear scans have a same resolution as the corresponding higher resolution cochlear scans.

5. The method of claim 1, wherein the generic predetermined frequency function comprises:

$$f_{BM} = 2^{\frac{(0.0285N-0.1978)\theta+168+c}{12}}$$

wherein N comprises the number of turns, θ comprises the angle in degrees as measured from a cochlear round window, $f_{BM}$ comprises a frequency response of the basilar membrane at the angle, and c comprises:

$c=-1.26-2.33 \cos(0.0059\theta)-6.84 \sin(0.0059\theta)$; or wherein the generic predetermined frequency function is generated from synchrotron radiation-phase contrast imaging scans of a plurality of cochleae and basilar membranes.

6. The method of claim 1, wherein determining, from the higher resolution image, the number of turns of the cochlea comprises one or more of:

segmenting the higher resolution image;

identifying edges of the cochlea in the higher resolution image;

performing shape analysis on the higher resolution image; and performing geometric analysis on the higher resolution image.

7. The method of claim 1, wherein determining, from the higher resolution image, the number of turns of the cochlea comprises analyzing the higher resolution image to determine estimations of one or more of:

a modiolar axis of the cochlea;

a basal plane of the cochlea;

a length of a hook of the cochlea;

a position of a helicotrema of the cochlea; and a respective position of a round window of the cochlea.

8. The method of claim 1, wherein the clinically available scan further comprises a preoperative clinically available scan for planning insertion of a cochlear implant into the cochlea, and the higher resolution image comprises one or more of a preoperative higher resolution image and a preoperative higher resolution segmentation, the preoperative clinically available scan, the preoperative higher resolution image, and the preoperative higher resolution segmentation including one more of:

a temporal bone;

an external auditory canal;

ossicles;

a tympanic membrane;

an inner ear;

a round window;

a facial nerve;

a chorda tympani nerve; a a sigmoid sinus;

a carotid artery; and a tegmen.

9. The method of claim 1, wherein inputting the clinically available scan of the cochlea to the machine learning engine comprises, prior to the inputting: generating an upsampled version of the clinically available scan, the upsampled version of the clinically available scan used as input to the machine learning engine, and the upsampled version having a same resolution as one or more of the higher resolution image and respective higher resolution cochlear scans used to train the machine learning engine.

10. The method of claim 1, wherein the higher resolution image comprises a higher resolution segmentation of the cochlea.

11. A device comprising:

a controller configured to:

input a clinically available scan, of a cochlea of a given format, to a machine learning engine trained to: output higher resolution cochlear images of a resolution higher than the given format using input based on clinically available cochlear scans of the given format;

determine, using the machine learning engine, a higher resolution image of the cochlea;

determine, from the higher resolution image, a number of turns of the cochlea; and one or more of determine, and output, a frequency function of a basilar membrane of the cochlea that is dependent on an angle of the basilar membrane, by inputting the number of turns into a generic predetermined frequency function dependent on the number of turns and the angle.

12. The device of claim 11, wherein the clinically available scan comprises a preoperative clinically available scan, and the higher resolution image comprises a preoperative higher resolution image, the controller is further configured to:

input a postoperative clinically available scan of the cochlea of the given format to the machine learning engine, the postoperative clinically available scan including an image of a cochlear implant inserted into the cochlea;

determine, using the machine learning engine, a postoperative higher resolution image of the cochlea and the cochlear implant;

determine, from the postoperative higher resolution image, respective positions of electrodes of the cochlear implant; and tune the electrodes of the cochlear implant based on the respective positions of the electrodes and the frequency function.

13. The device of claim 12, wherein the controller is further configured to determine the respective positions of the electrodes of the cochlear implant by:

aligning the postoperative clinically available scan with the preoperative higher resolution image; and determining the respective positions of the electrodes of the cochlear implant at the preoperative higher resolution image.

14. The device of claim 11, wherein the controller is further configured to train the machine learning engine in a training mode using:

as training input to the machine learning engine, one or more of the clinically available cochlear scans of the given format and upsampled versions of the clinically available cochlear scans; wherein the given format comprises one or more of helical computerized tomography (CT) scans and cone beam CT scans; and as training output to the machine learning engine, corresponding higher resolution cochlear scans, the corresponding higher resolution cochlear scans comprising one or more of corresponding higher resolution cochlear images and corresponding higher resolution cochlear segmentations, the corresponding higher resolution cochlear scans based on one or more of synchrotron radiation-phase contrast imaging scans and micro-CT scans; wherein the upsampled versions of the clinically available cochlear scans have a same resolution as the corresponding higher resolution cochlear scans.

15. The device of claim 11, wherein the generic predetermined frequency function comprises:

$$f_{BM} = 2^{\frac{(0.0285N - 0.1978)\theta + 168 + c}{12}}$$

wherein N comprises the number of turns, $\theta$ comprises the angle in degrees as measured from a cochlear round window, $f_{BM}$ comprises a frequency response of the basilar membrane at the angle, and c comprises:

$$c = -1.26 - 2.33 \cos(0.0059\theta) - 6.84\sin(0.0059\theta);$$

or wherein the generic predetermined frequency function is generated from synchrotron radiation-phase contrast imaging scans of a plurality of cochleae and basilar membranes.

16. The device of claim 11, wherein the controller is further configured to determine, from the higher resolution image, the number of turns of the cochlea by one or more of:

segmenting the higher resolution image;

identifying edges of the cochlea in the higher resolution image;

performing shape analysis on the higher resolution image; and performing geometric analysis on the higher resolution image.

17. The device of claim 11, wherein the controller is further configured to determine, from the higher resolution image, the number of turns of the cochlea comprises analyzing the higher resolution image to determine estimations of one or more of:

a modiolar axis of the cochlea;

a basal plane of the cochlea;

a length of a hook of the cochlea;

a position of a helicotrema of the cochlea; and a respective position of a round window of the cochlea.

18. The device of claim 11, wherein the clinically available scan further comprises a preoperative clinically available scan for planning insertion of a cochlear implant into the cochlea, and the higher resolution image comprises one or more of a preoperative higher resolution image and a preoperative higher resolution segmentation, the preoperative clinically available scan, the preoperative higher resolution image, and the preoperative higher resolution segmentation including one more of:

a temporal bone;

an external auditory canal;

ossicles;

a tympanic membrane;

an inner ear;

a round window;

a facial nerve;

a chorda tympani nerve; a a sigmoid sinus;

a carotid artery; and a tegmen.

19. The device of claim 11, wherein inputting the clinically available scan of the cochlea to the machine learning engine comprises, prior to the inputting: generating an upsampled version of the clinically available scan, the upsampled version of the clinically available scan used as input to the machine learning engine, and the upsampled version having a same resolution as one or more of the higher resolution image and respective higher resolution cochlear scans used to train the machine learning engine.

20. The device of claim 11, wherein the higher resolution image comprises a higher resolution segmentation of the cochlea.

\* \* \* \* \*